United States Patent
Matsunaga et al.

(10) Patent No.: US 10,791,968 B2
(45) Date of Patent: Oct. 6, 2020

(54) INFORMATION PROCESSING DEVICE, SENSOR DEVICE, INFORMATION PROCESSING SYSTEM, AND STORAGE MEDIUM

(71) Applicant: SONY CORPORATION, Tokyo (JP)

(72) Inventors: Hideyuki Matsunaga, Kanagawa (JP); Kosei Yamashita, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 120 days.

(21) Appl. No.: 16/209,995

(22) Filed: Dec. 5, 2018

(65) Prior Publication Data

US 2019/0150797 A1    May 23, 2019

Related U.S. Application Data

(63) Continuation of application No. 14/149,265, filed on Jan. 7, 2014, now Pat. No. 10,188,324.

(30) Foreign Application Priority Data

Mar. 22, 2013   (JP) ................................ 2013-060062

(51) Int. Cl.
*A61B 5/11* (2006.01)
*G01P 15/00* (2006.01)
(Continued)

(52) U.S. Cl.
CPC ............ *A61B 5/1126* (2013.01); *G01P 15/00* (2013.01); *G06K 9/00342* (2013.01);
(Continued)

(58) Field of Classification Search
None
See application file for complete search history.

(56) References Cited

U.S. PATENT DOCUMENTS 4,257,594 A * 3/1981 Conrey .............. A63B 24/0021
                                                        473/463
4,991,850 A * 2/1991 Wilhlem ............ A63B 69/3632
                                                        473/233
(Continued)

FOREIGN PATENT DOCUMENTS

CN       102814033 A    12/2012
EP       2 532 396 A1   12/2012
(Continued)

OTHER PUBLICATIONS

Office Action dated Dec. 20, 2016 in Japanese Patent Application No. 2015-173874.
(Continued)

*Primary Examiner* — John C Kuan
(74) *Attorney, Agent, or Firm* — Xsensus LLP

(57) ABSTRACT

An information processing system inclines processing circuitry that is configured to receive input data from a shock sensor which outputs data based on a shock on the shock sensor, and identify a target segment of time-series data that is output from a motion sensor that senses a motion of an object. The target segment includes a pre-shock portion that occurs before the shock event and a post-shock portion that occurs after the shock event, the shock event is recognized based on the data from the shock sensor.

20 Claims, 20 Drawing Sheets

(51) Int. Cl.
  *A63B 24/00* (2006.01)
  *G06K 9/00* (2006.01)
  *G09B 19/00* (2006.01)
  *A63B 71/06* (2006.01)

(52) U.S. Cl.
  CPC ...... *G09B 19/0038* (2013.01); *A63B 24/0003* (2013.01); *A63B 71/0619* (2013.01); *A63B 2024/0012* (2013.01); *A63B 2024/0037* (2013.01); *A63B 2024/0043* (2013.01); *A63B 2024/0056* (2013.01)

(56) References Cited

U.S. PATENT DOCUMENTS

| | | | |
|---|---|---|---|
| 5,031,909 A * | 7/1991 | Pecker | A63B 69/38 473/224 |
| 5,757,266 A * | 5/1998 | Rider | A63B 69/38 273/317.4 |
| 6,196,932 B1 * | 3/2001 | Marsh | A63B 24/0021 473/223 |
| 7,736,242 B2 | 6/2010 | Stites et al. | |
| 2001/0053720 A1 | 12/2001 | Lee et al. | |
| 2002/0123386 A1 | 9/2002 | Perlmutter | |
| 2003/0032494 A1 * | 2/2003 | McGinty | A63B 69/3623 473/222 |
| 2005/0215340 A1 * | 9/2005 | Stites | A63B 60/42 473/233 |
| 2005/0282645 A1 * | 12/2005 | Bissonnette | A63B 24/0021 473/131 |
| 2006/0052173 A1 | 3/2006 | Telford | |
| 2006/0084516 A1 | 4/2006 | Eyestone et al. | |
| 2006/0184336 A1 | 8/2006 | Kolen | |
| 2007/0105664 A1 * | 5/2007 | Scheinert | A63B 69/38 473/461 |
| 2007/0219744 A1 | 9/2007 | Kolen | |
| 2010/0304877 A1 * | 12/2010 | Iwahashi | A63B 69/3632 473/223 |
| 2011/0021280 A1 * | 1/2011 | Boroda | A63B 60/46 473/220 |
| 2011/0183787 A1 * | 7/2011 | Schwenger | A63B 49/02 473/553 |
| 2011/0305369 A1 | 12/2011 | Bentley et al. | |
| 2012/0316004 A1 | 12/2012 | Shibuya | |
| 2013/0053190 A1 * | 2/2013 | Mettler | A63B 49/00 473/463 |
| 2013/0158939 A1 | 6/2013 | Yamamoto | |
| 2013/0267339 A1 | 10/2013 | Boyd et al. | |
| 2013/0316855 A1 * | 11/2013 | Mace | A63B 69/38 473/422 |
| 2014/0260636 A1 | 9/2014 | Kammerer et al. | |

FOREIGN PATENT DOCUMENTS

| | | | |
|---|---|---|---|
| JP | 3134032 A | | 6/1995 |
| JP | 2006129980 A | * | 5/2006 |
| JP | 2009-125499 A | | 6/2009 |
| JP | 2011-242323 A | | 12/2011 |
| JP | 2011-251041 A | | 12/2011 |
| JP | 2012-120579 A | | 6/2012 |
| JP | 2012-130414 A | | 7/2012 |
| JP | 2012-130415 A | | 7/2012 |
| JP | 2012-157644 A | | 8/2012 |
| JP | 2013-009917 A | | 1/2013 |
| WO | 2006/088863 A2 | | 8/2006 |
| WO | 2013/136712 A1 | | 9/2013 |
| WO | 2014/097579 A1 | | 6/2014 |

OTHER PUBLICATIONS

Maurer et al., "Activity Recognition and Monitoring Using Multiple Sensors on Different Body Positions" Proceedings of the International Workshop on Wearable and Implantable Body Sensor Networks (BSN'06), 2006 IEEE.

Partial European Search Report dated Nov. 3, 2014 in the corresponding European Application No. 14159893.8.

Damien Connaghan, et al., "Multi-Sensor Classification of Tennis Strokes", 2011 IEEE Sensors Proceedings, XP032277439, Oct. 28, 2011, pp. 1437-1440.

Cao Nguyen Khoa Nam, et al., "Golf Swing Motion Tracking Using Inertial Sensors and a Stereo Camera", IEEE Transactions on Instrumentation and Measurement, vol. 63, No. 4, XP011542295, Apr. 1, 2014, pp. 943-952.

Extended European Search Report dated Feb. 19, 2015 in Patent Application No. 14159893.8.

Office Action dated Apr. 28, 2015 in Japanese Patent Application No. 2013-060062.

Combined Chinese Office Action and Search Report dated Mar. 28, 2016 in Patent Application No. 201410097086.4 (with English language translation).

Oconaire, C., et al. "Combining Inertial and Visual Sensing for Human Action Recognition in Tennis", Artemis 10, pp. 51-56, (Oct. 29, 2010).

Slyper, R., et al. "Action Capture with Accelerometers", EUROGRAPHICS/ACM SIGGRAPH Symposium on Computer Animation, 7 Pages total, (2008).

* cited by examiner

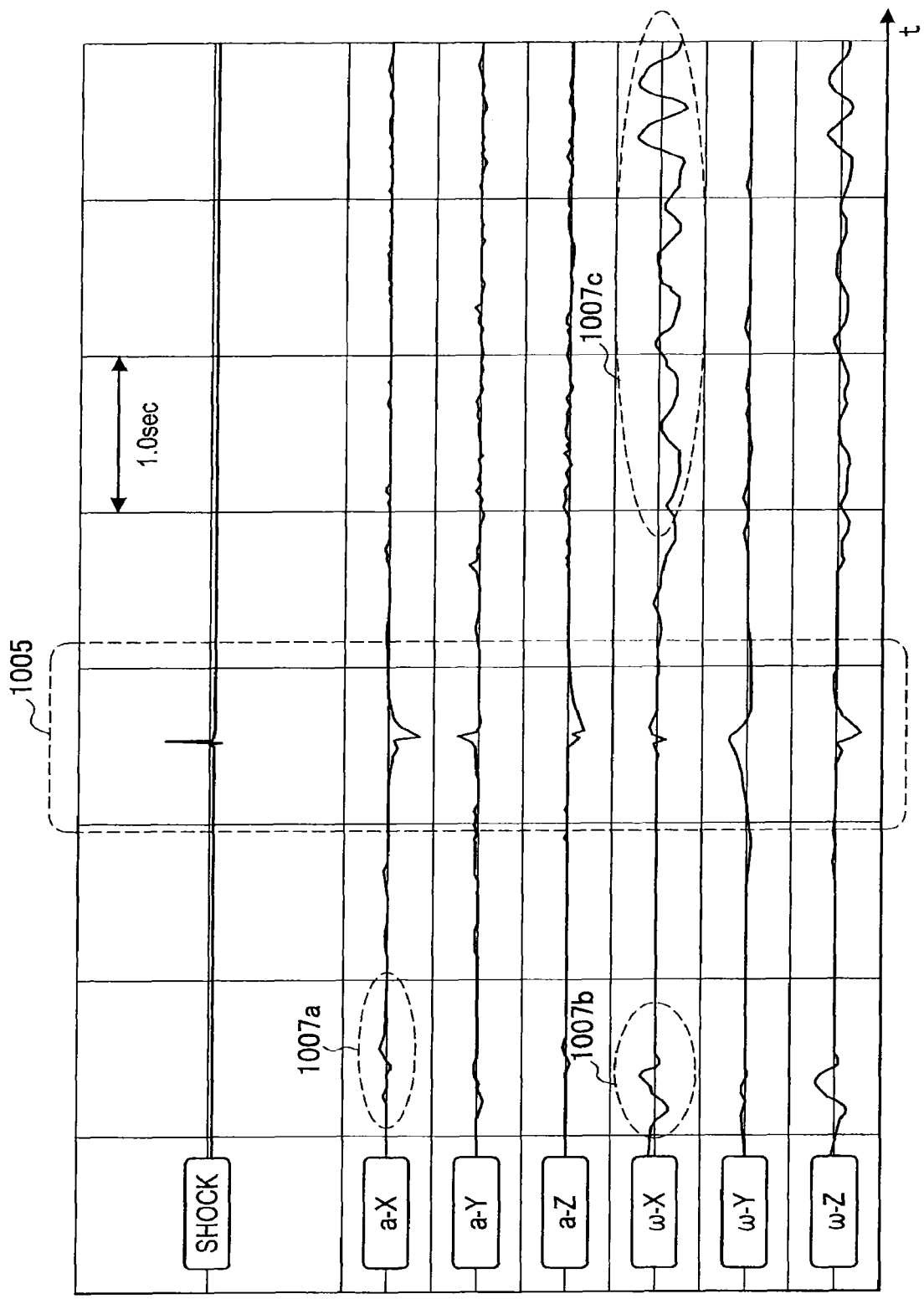

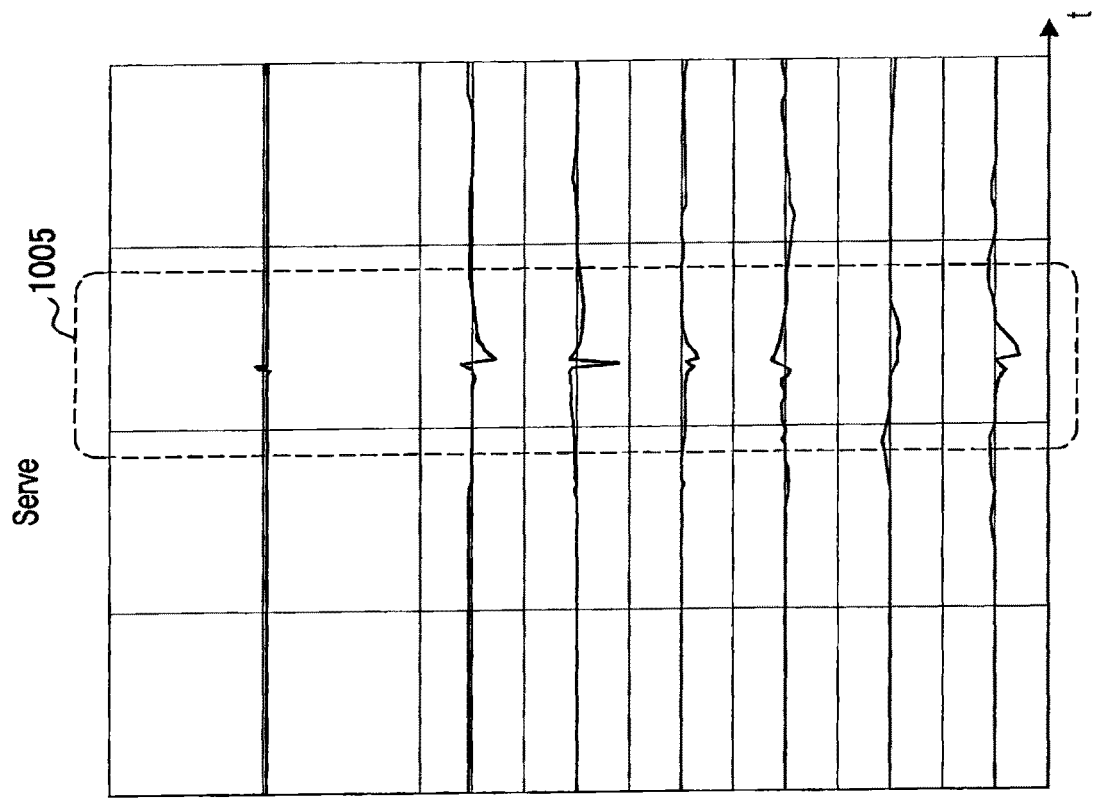
FIG. 10A Forehand Stroke
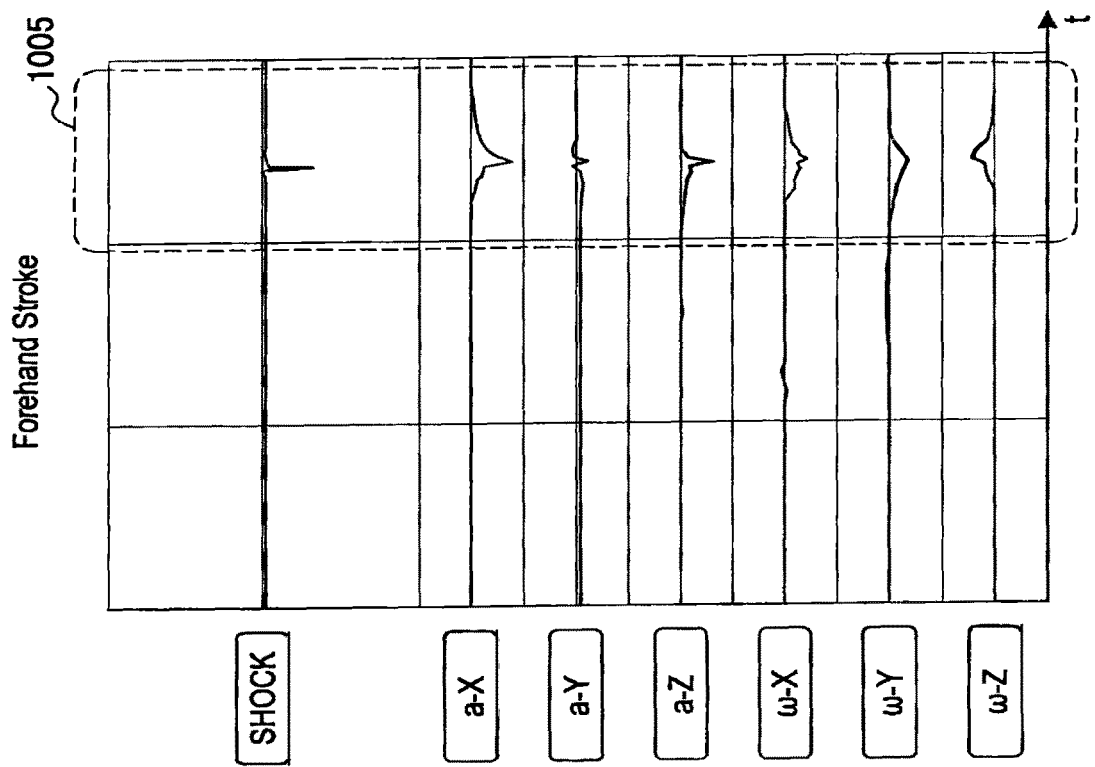
FIG. 10B Serve

FIG.12
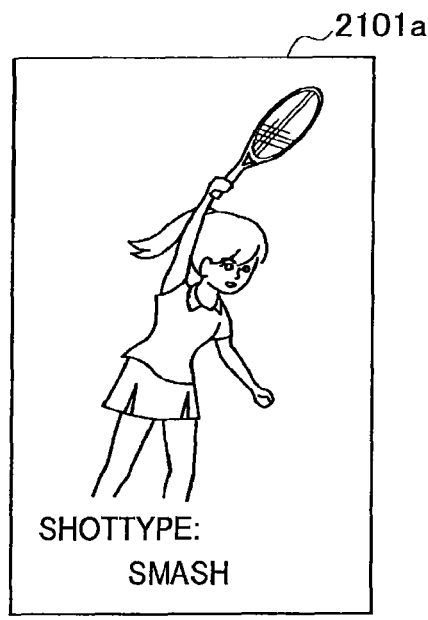
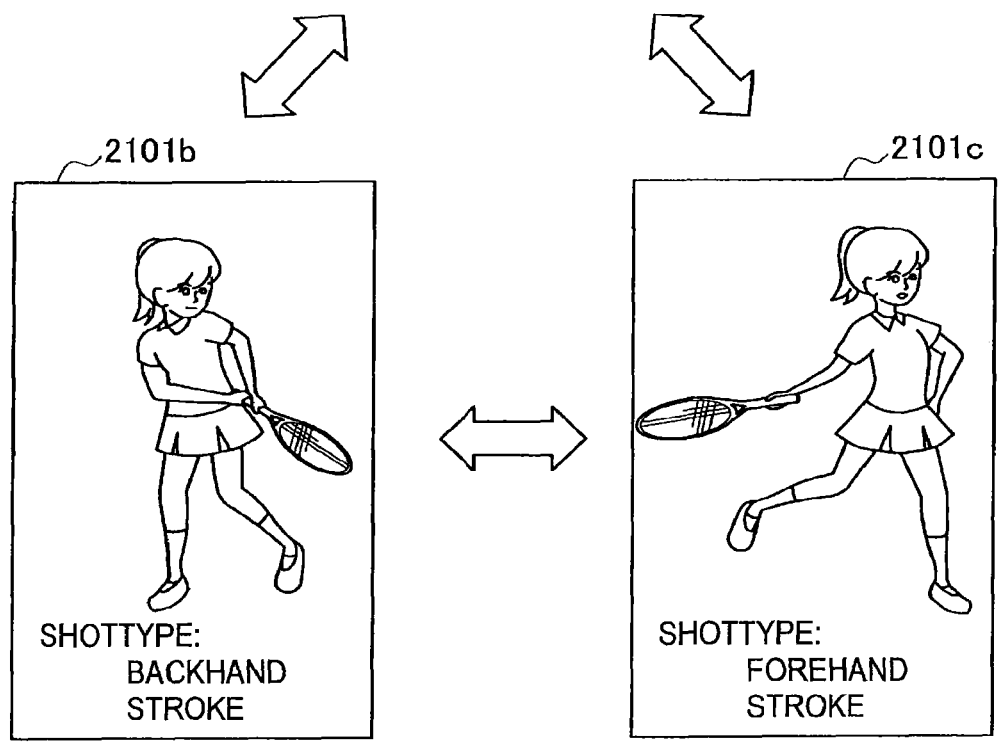

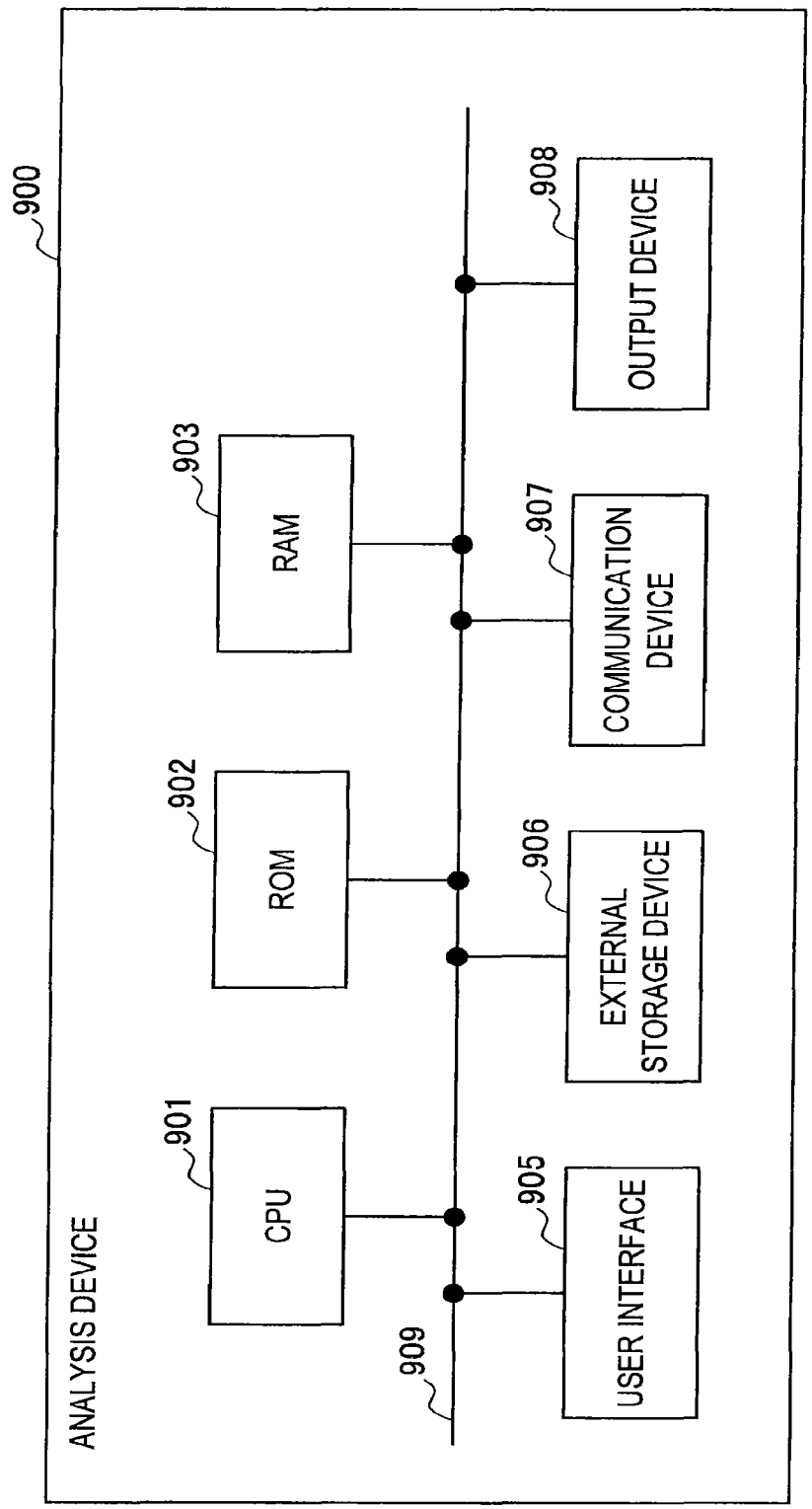

INFORMATION PROCESSING DEVICE, SENSOR DEVICE, INFORMATION PROCESSING SYSTEM, AND STORAGE MEDIUM

CROSS-REFERENCE TO RELATED APPLICATIONS

This Application is a continuation of U.S. application Ser. No. 14/149,265, filed on Jan. 7, 2014, which claims the benefit of Japanese Priority Patent Application JP 2013-060062, filed on Mar. 22, 2013, the entire contents of which are incorporated herein by reference.

BACKGROUND

The present technology relates to an information processing device, a sensor device, an information processing system, and a storage medium.

Up to the present, many technologies for assisting users in becoming proficient at sports using sensing or analysis have been developed. In the technologies, statistical analysis of plays of users themselves or other users is used as one method. In the statistical analysis of plays, determination of motion patterns in plays can be useful in, for example, bell sports. Motion patterns arc obtained by patterning specific motions shown in plays of sports. For example, in the case of tennis, motion patterns can be set for plays such as a serve, a smash, a forehand stroke, and a backhand stroke. By determining the motion patterns observed in plays, for example, how a user makes a play can be quantitatively expressed with ease.

The determination of motion patterns in such sports has heretofore been performed by supporters of users' plays such as coaches, scorers, or managers. The supporters visually confirm users' plays and record specific motions upon observation. For such man-powered notion analysis, much effort is necessary. Further, it is difficult for users playing sports to perform the motion analysis on their own.

Accordingly, technologies for automatically analyzing motions by attaching sensor devices on which acceleration sensors, gyro sensors, or the like are mounted on users or equipment used by the users and analyzing data output from the sensors have been suggested. For example, Japanese Unexamined Patent Application Publication No. 2012-157641, Japanese Unexamined Patent Application Publication No. 2012-130415, and Japanese Unexamined Patent Application Publication No. 2012-120579 disclose technologies for extracting feature information of swings based cm data output from motion sensors.

SUMMARY

For example, in the technology disclosed in Japanese Unexamined Patent Application Publication No. 2012-157644, a process of searching for timings of segments of a swing appearing in data output from a motion sensor is performed before feature information of the swing is extracted. In this case, however, a processing load may be increased since the process of searching for segments corresponding to feature motions in the data output from the motion sensor is repeated. Further, accuracy of the determination of a motion pattern is not high either since setting of the segments is not stable. Japanese Unexamined Patent Application Publication No. 2012-130415 and Japanese Unexamined Patent Application Publication No. 2012-120579 do not suggest improvement countermeasures for this problem either.

It is desirable to provide a novel and improved information processing device, a novel and improved sensor device, a novel and improved information processing system, and a novel and improved storage medium capable of improving accuracy of determination by suitably setting segments to be analyzed when detection values of a sensor detecting a physical behavior of a sensor device are analyzed and a motion pattern of a user is determined.

According to one embodiment, an information processing system is described the includes processing circuitry configured to receive input data from a shock sensor which outputs data based on a shock on the shock sensor, and identify a target segment of time-series data that is output from a motion sensor that senses a motion of an object, wherein the target segment includes a pre-shock portion that occurs before a shock event and a post-shock portion that occurs after the shock event, the shock event is recognized based on the data from the shock sensor.

According to a method embodiment, the method includes receiving input data from a shock sensor which is configured to output data based on a shock on the shock sensor;

receiving time-series data from a motion sensor that senses motion of an object; and identifying with processing circuitry a target segment of the time-series data, wherein the target segment includes a pre-shock portion that occurs before a shock event and a post-shock portion that occurs after the shock event, the shock event is recognized based on the data from the shock sensor.

According to a non-transitory computer readable storage device embodiment, the device includes instructions that when executed by a processor configure the processor to implement an information processing method, the method comprising:

receiving input data from a shock sensor which is configured to detect a shock event;

receiving time-series data from a motion sensor that senses motion of an object; and identifying with processing circuitry a target segment of the time-series data, wherein the target segment includes a pre-shock portion that occurs before the shock and a post-shock portion that occurs after the shock.

BRIEF DESCRIPTION OF THE DRAWINGS

FIG. 9 is a graph illustrating a specific example of sensor data according to an embodiment of the present technology;

FIGS. 10A and 10B are graphs illustrating specific examples of sensor data according to an embodiment of the present technology;

FIG. 12 is a diagram illustrating other examples of motion pattern displays according to an embodiment of the present technology;

FIG. 20 is a diagram illustrating an example of a hardware configuration of an analysis device according to an embodiment of the present technology.

DETAILED DESCRIPTION OF THE EMBODIMENTS

Figure 1:
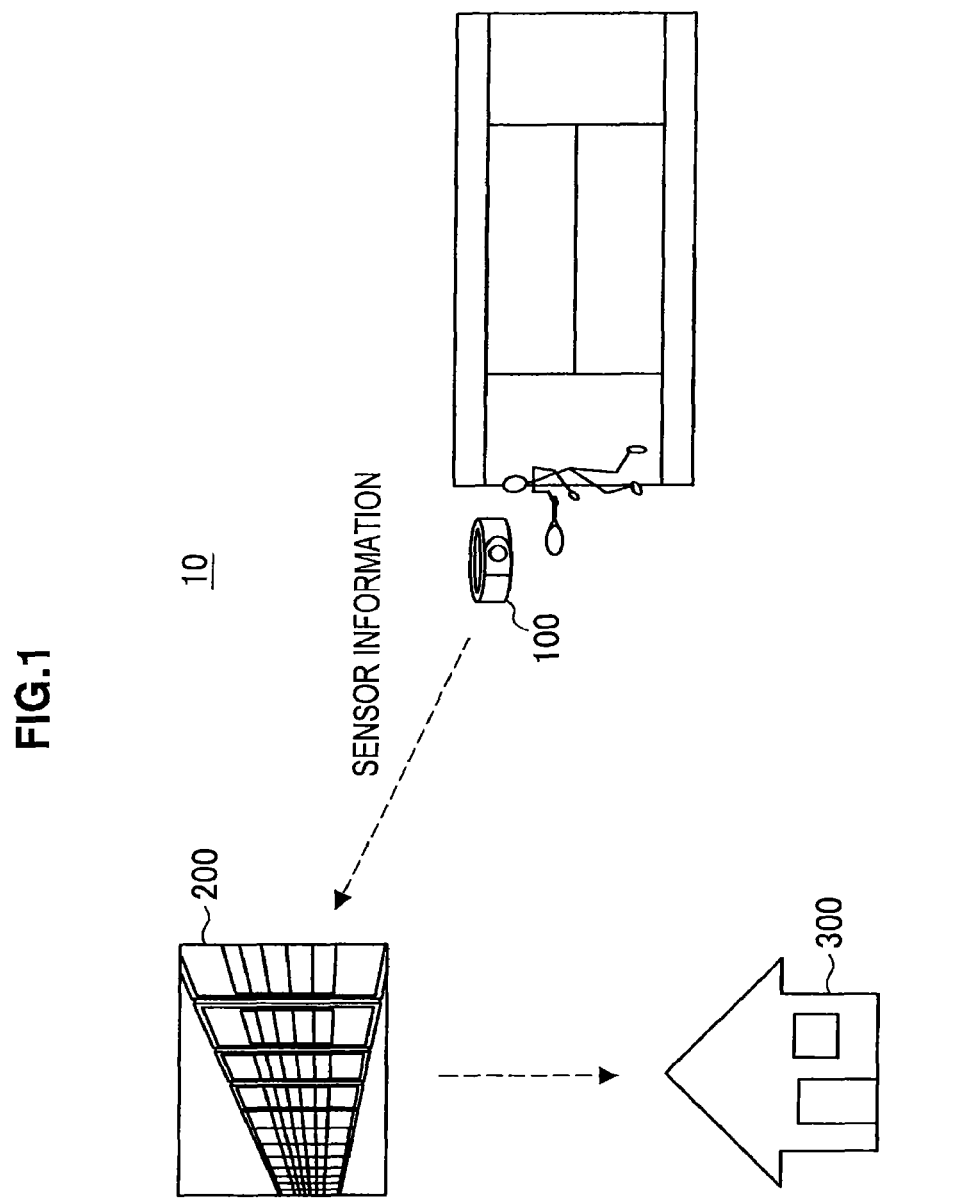
FIG. 1 is a diagram illustrating the overview of an information processing system according loan embodiment of the present technology.

Hereinafter, preferred embodiments of the present disclosure will be described in detail with reference to the appended drawings. Note that, in this specification and the appended drawings, structural elements that have substantially the same function and structure are denoted with the same reference numerals, and repealed explanation of these structural elements is omitted.

The description will be made in the following order.
1. Overview
2. Functional configuration
3. Processing How
4. Specific example
5. Example of output information
6. Hardware configuration
7. Supplement (1. Overview)

First, the overview of an embodiment of the present technology will be described with reference to FIGS. 1 and 2. The description of the overview includes description of the overview of an information processing system according to the embodiment and description of the overview of a motion identification process performed by the information processing system.

(Overview of Information Processing System)

FIG. 1 is a diagram illustrating the overview of the information processing system according to the embodiment of the present technology. Referring to FIG. 1, an information processing system 10 includes a sensor device 100 and an analysis device 200.

The sensor device 100 is mounted directly or indirectly on a user who plays sports. When the sensor device 100 is mounted directly on the user, for example, as illustrated in the drawing, the sensor device 100 may be configured to have a wristlet shape and may be mounted directly on the body of the user. When the sensor device 100 is mounted indirectly on the user, the sensor device 100 may be wound around, sewn on, or attached to sports equipment (for example, a racket, clothing, shoes, a wristband, or the like in a case of tennis) which the user holds or wears or may be included in equipment in advance.

Here, the sensor device 100 acquires sensor information indicating a physical behavior (a position, a speed an acceleration, or the like) of the sensor device 100 itself. A physical behavior of the user or equipment is reflected in the sensor information. In this embodiment, the sensor device 100 includes at least two sensors to acquire such sensor information. A first sensor of the sensor device 100 detects a shock transferred from the user or the equipment. The first sensor may include, for example, a uniaxial acceleration sensor used as a shock sensor. On the other hand, a second sensor detects a behavior of the sensor device 100 with a higher resolution than that of the first sensor. The second sensor may include, for example, a triaxial acceleration sensor, a gyro sensor, and a geomagnetic sensor used as motion sensors. The sensor device 100 may further include one sensor or a plurality of sensors that detect an acceleration, an angular speed, vibration, a temperature, a time, or a position (for example, a position on the surface of ground expressed by a latitude and a longitude or a relative position to a court or the like) in addition to the first and second sensors. The sensor device 100 transmits time-series data obtained from such sensors to the analysis device 200.

The analysis device 200 analyses the time-series data transmitted from the sensor device 100 to determine at least a motion pattern of a user. The analysis device 200 is illustrated as a server on a network. However, for example, any device may be used as long as the analysis device 200 is an information processing device that has a function of analyzing data through calculation using a processor a central processing unit (CPU) or the like. As another example, the analysis device 200 may be, for example, a terminal device such as a smartphone, a tablet terminal, or various personal computers (PCs). When the analysis device 200 is realized as a terminal device, the analysis device 200 may output information indicating the determined motion pattern of the user. Alternatively, when the analysis device 200 is realized as a server, the analysis device 200 may transmit the information indicating the determined motion pattern of the user to, for example, a client 300 such as a terminal device used in a house by the user. Based on the determination result of the motion pattern, the analysis device 200 may output statistical information indicating, for example, how many times the user performs a motion or may output information indicating a tendency (for example, a position of a ball hit by equipment, power or rotation given to a ball, or the like in a case of ball sports) of the user in each motion.

When the analysis device 200 is realized as a server as in the example illustrated in the drawing, the function of the server may be realized by a single server device or may be distributed and realized by a plurality of server devices connected via a network. Further, the function of the analysis device 200 may be distributed and realized in a server and a terminal device connected via a network.

(Overview of Motion Pattern Determination Process)

Figure 2:
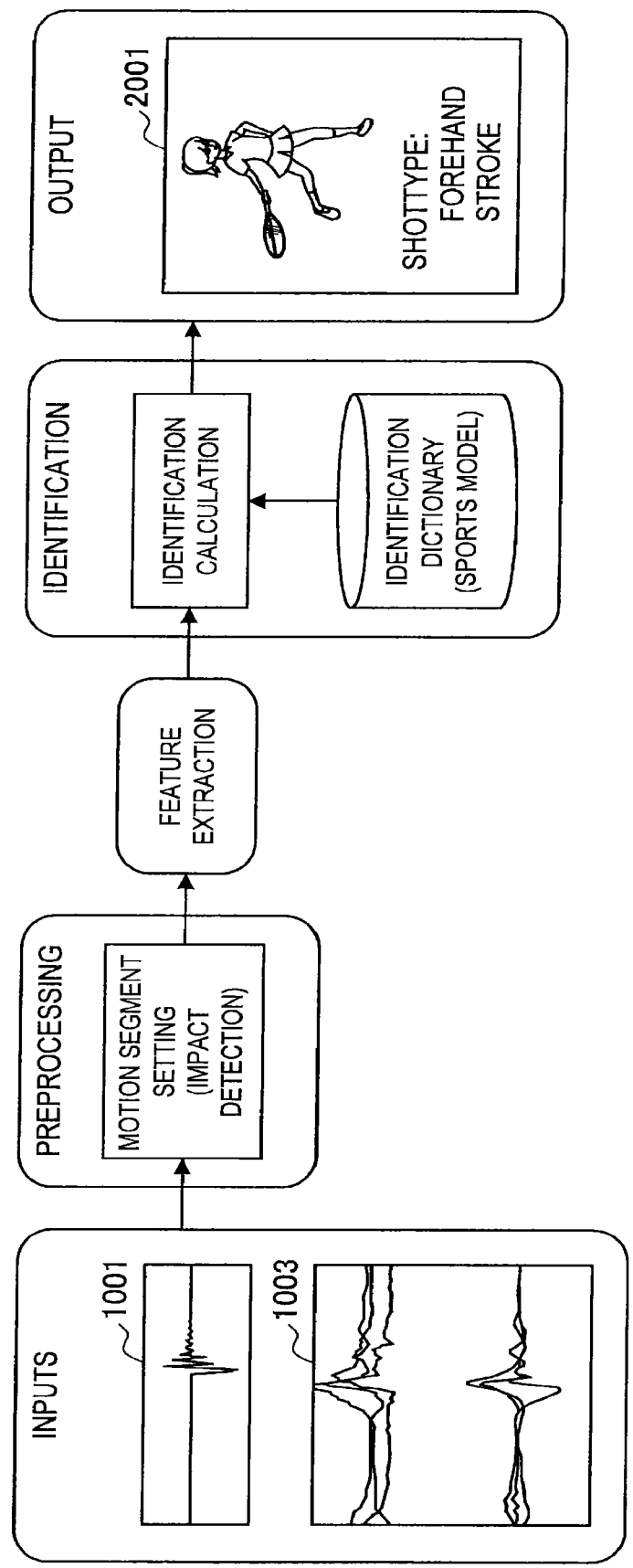
FIG. 2 is a diagram illustrating the overview of a motion pattern determination process according to an embodiment of the present technology.

FIG. 2 is a diagram illustrating the overview of a motion pattern determination process according to the embodiment of the present technology. In the motion pattern determination process, as illustrated in FIG. 2, time-series data 1001 and time-series data 1003 output from the two sensors included in the sensor device 100 are used as inputs.

In the example illustrated in the drawing, the time-series data 1001 includes data output from the first acceleration sensor (uniaxial). The first acceleration sensor is a so-called shock sensor. The first acceleration can detect an acceleration having a larger dynamic range and a relatively high frequency occurring due to a shock, whereas the resolution of the acceleration is not particularly high. On the other hand, the time-series data 1003 includes data output from the second acceleration sensor (triaxial). The second acceleration sensor is a so-called motion sensor. The second acceleration sensor can detect an acceleration with a relatively low frequency containing a stationary component like the force of gravity and has a high resolution of the acceleration, whereas the dynamic range is relatively narrow (there is a probability of an acceleration that occurs due to a shock exceeding a detectable range).

In identification calculation for determining a motion pattern, the time-series data 1003 with high resolution is basically used. Further, in this embodiment, a motion segment setting process (impact detection process) is performed as preprocessing using the lime-series data 1001. In the motion segment setting process, an analysis target segment in the time-series data 1003 is set based on the time-series data 1001. That is, through the preprocessing, an identification calculation target in the time-series data 1003 is restricted to the analysis target segment set based on the time-series data 1001.

In many sports, a feature motion which is a motion pattern determination target may be, for example, hitting of a ball by equipment or the body of a user, stomping of a user on the surface of the ground, or colliding with another user. Since such a motion causes a shock applied to a user or equipment and vibration occurring due to the impact, portions on either side of a point at which vibration is detected in die time-series data 1001 of the shock sensor can be specified as segments (motion segments) corresponding to a motion.

After the motion segment setting process, the features of the time-series data 1003 are extracted from the set analysis target segment. Here, for example, frequency features of a signal waveform or statistical features of a time waveform such as an average, a dispersion, a minimum value, and a maximum value are extracted by performing signal processing on the time-series data 1003. For example, FIGS. 10A and 10B illustrate sensor output waveforms at the time of a forehand stroke and a serve. In comparison of the waveforms, particularly, features are different in amplitudes of time waveforms such as ω-X and ω-Z. Before the extraction of the features, missing portions of signal waveforms may be interpolated. The extracted features may be subjected to a statistical process such as normalization.

Subsequently, the extracted features are subjected to identification calculation. The identification calculation is a calculation process of identifying a motion by specifying a motion pattern corresponding to the extracted features with reference to an identification dictionary (sports model) prepared beforehand. For example, the identification dictionary may be generated for each sport and classifications may be switched by setting of a user. As the identification calculation, for example, a non-rule based method of forming identification parameters from data by machine learning such as a neural network, a Support Vector Machine (SVM), a k-neighborhood identifier, and Bayes' classification can be used.

As in the time-series data 1003, features may be extracted from the time-series data 1001 and the extracted features may be used for the identification calculation. That is, the time-series data 1001 of the shock sensor may he used not only in the setting of the motion segment but also in the identification calculation along with the time-series data 1003 of the motion sensor.

When the determination of the motion pattern succeeds as a result of the identification calculation, motion pattern information 2001 is output. The motion pattern information 2001 is, for example, information for notifying a user of a motion pattern (in the example illustrated in the drawing, a shot type of tennis=forehand stroke is shown), as illustrated in the drawing, and may further include the above-described statistical information or information indicating a tendency of the user.

Examples of definition of motion patterns are shown in the following Table 1. Thus, motion patterns may be defined for each sport or may be defined for a category of sports. The foregoing identification dictionary may be generated for each sport or category of sports and the sport or the category of sports may be switched by setting of a user. The motion patterns shown here are merely examples, and thus various types of motion patterns can be defined in various other sports.

TABLE 1

| ITEM | TYPE | PATTERN DETAILS |
|---|---|---|
| TENNIS | SWINGS | FOREHAND STROKE |
|  |  | FOREHAND VOLLEY |
|  |  | FOREHAND SLICE |
|  |  | BACKHAND STROKE |
|  |  | BACKHAND VOLLEY |
|  |  | BACKHAND SLICE |
|  |  | SMASH |
|  |  | SERVE |
| BASEBALL | SWINGS | UPPER SWING |
|  |  | LEVEL SWING |
|  |  | DOWN SWING |
|  |  | BUNT |
| SOCCER | SHOTS | SHOT |
|  |  | LOB SHOT |
|  |  | DRIVE SHOT |
|  |  | VOLLEY SHOT |
|  |  | OVERHEAD SHOT |
| TABLE TENNIS | SWINGS | FOREHAND |
|  |  | FOREHAND CUT |
|  |  | FOREHAND DRIVE |
|  |  | BACKHAND |
|  |  | BACKHAND CUT |
|  |  | BACKHAND DRIVE |
|  |  | SERVE |

(2. Functional Configuration)

Next, functional configurations of devices included in the information processing system according to the embodiment of the present technology will he described with reference to FIGS. 3 and 4.

Figure 3:
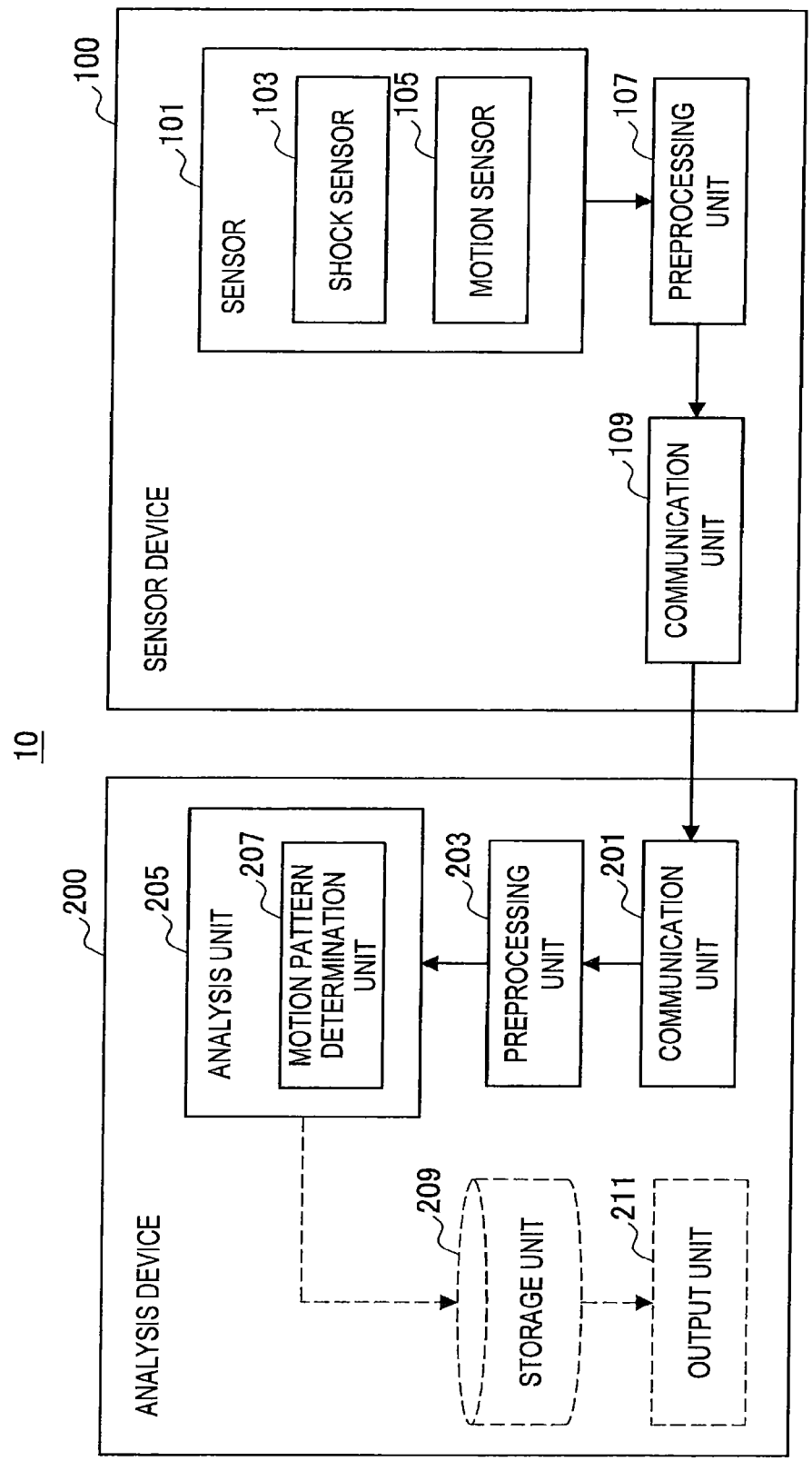
FIG. 3 is a block diagram illustrating a schematic functional configuration of an information processing system according to an embodiment of the present technology.

FIG. 3 is a block diagram illustrating a schematic functional configuration of the information processing system according to the embodiment of the present technology. Hereinafter, the functional configurations of each device will be described with reference to FIG. 3. A hardware configuration for realizing the functions will be described later.

(Sensor Device)

The sensor device 100 includes a sensor 101, a preprocessing unit 107, and a communication unit 109.

The sensor 101 includes a shock sensor 103 and a motion sensor 105. The shock sensor 103 is the first sensor that detects a shock transferred from a user or equipment in the sensor device 100 and may include a uniaxial acceleration sensor according to this embodiment. The motion sensor 105 is the second sensor that detects a behavior of the sensor device 100 at a resolution higher than that of the first sensor and may include it triaxial acceleration sensor, a gyro sensor, or a geomagnetic sensor in this embodiment. The sensor 101 may further include another sensor such as a temperature sensor, a clock, or a Global Positioning System (GPS) receiver in addition to the shock sensor 103 and the motion sensor 105.

Here, differences between the shock sensor 103 and the motion sensor 105 included in the sensor 101 will be described further with reference to FIG. 4. FIG. 4 is a diagram illustrating the shock sensor and the motion sensor according to the embodiment of the present technology. In the following description, a case in which both of the shock sensor 103 and the motion sensor 105 are acceleration sensors will be described, but the same applies to a case in which other types of sensors are used.

Figure 4:
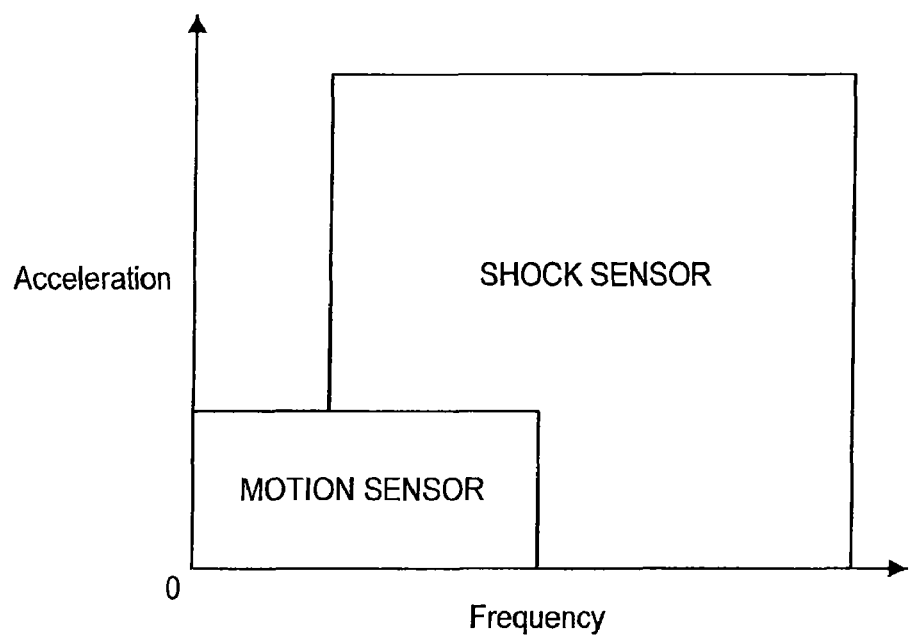
FIG. 4 is a diagram for describing a shock sensor and a motion sensor according to an embodiment of the present technology.

Referring to FIG. 4, the shock sensor 103 has a larger dynamic range of acceleration values than the motion sensor 105. For example, the shock sensor 103 can detect a large acceleration instantaneously occurring due to a shock applied to a user or equipment. However, the resolution of the acceleration of the shock sensor 103 is lower than that of the motion sensor 105. Further, the shock sensor 103 does not detect an acceleration change of a low frequency. For example, an acceleration change occurring when a user swings a part of the body or equipment on which the sensor device 100 is mounted is not detected by the shock sensor 103, since a frequency is low. Further, since the acceleration caused due to the force of gravity of the earth is a stationary component which does not vibrate, this acceleration is riot detected by the shock sensor 103. On the other hand, an acceleration change of a high frequency can be detected by the shock sensor 103, which can detect a higher frequency than the motion sensor 105. For example, a frequency component of an eigenfrequency of a user or equipment can be detected.

On the other hand, the motion sensor 105 has a narrower dynamic range of acceleration values than the shock sensor 103. Accordingly, for example, there is a probability of a large acceleration that occurs instantaneously due to a shock applied to a user or equipment exceeding a detectable range of the motion sensor 105. Further, with regard to a frequency of al acceleration change, the motion sensor 105 can merely detect a frequency lower than that of the shock sensor 103. However, the resolution of the acceleration of the motion sensor 105 is higher than that of the shock sensor 103 and acceleration data can be output to the degree of accuracy sufficient for motion pattern determination. Further, the motion sensor 105 can detect an acceleration change of a low frequency undetected by the shock sensor 103. For example, the motion sensor 105 can detect an acceleration change occurring when a user swings a part of the body or equipment on which the sensor device 100 is mounted. Further, the motion sensor 105 can also detect the acceleration caused due to the force of gravity of the earth. Accordingly, for example, by using a triaxial acceleration sensor as the motion sensor 105, it is possible to specify a direction of the acceleration occurring by setting the direction of the force of gravity as a reference.

The shock sensor 103 and the motion sensor 105 can be realized, for example, by changing the sensitivity or the number of axes of acceleration sensors operating on the same principle. These sensors can be realized, for example, using piezoresistance type or electrostatic capacitance type acceleration sensors. The sensitivity of the acceleration sensor used as the shock sensor 103 can be set to be lower than the sensitivity of the acceleration sensor used as the motion sensor 105. Of course, the shock sensor 103 and the motion sensor 105 may be realized by acceleration sensors that operate on different principles. As described above, the motion sensor 105 can further include a gyro sensor or a geomagnetic sensor.

Referring back to FIG. 3, the preprocessing unit 107 performs preprocessing on data detected by the sensor 101. The preprocessing can include, for example, amplification of the detected data or filtering of data equal to or less than a threshold value. Through such processing, the preprocessing unit 107 generate analysis target data to be transmitted to the analysis device 200 based on first time-series data including a detected value of the shock sensor 103 and second time series data including a detected value of the motion sensor 105.

In this embodiment, one of the preprocessing unit 107 of the sensor device 100 and a preprocessing unit 203 of the analysis device 200 functions as a segment setting unit. The segment setting unit sets an analysts target segment in the second time-series data including a detected value of the motion sensor 105 based on the first time-series data including a detected value of the shock sensor 103. In this process, the above-described motion segment setting is performed (an analysis target segment corresponds to a motion segment).

Here, when the preprocessing unit 107 functions as the segment setting unit, the preprocessing unit 107 may provide only the second time-series data in the set analysis target segment as the analysis target data to the communication unit 109. When a transmission target by the communication unit 109 is restricted to data of the analysis target segment, an effect of reducing power consumption by reduction in an amount of communication can be expected. Alternatively, the preprocessing unit 107 may generate separate data for indicating the detected analysis target segment using a time stamp or the like of the time-series data and provide the separate data as analysis target data together with the second time-series data to the communication unit 109.

However, when the preprocessing unit 203 of the analysis device 200 functions as the segment setting unit rather than the preprocessing unit 107, the preprocessing unit 107 associates the first time-series data and the second time-series data subjected to the above-described preprocessing with each other using, for example, a time stamp and provides the associated data as the analysis target data to the communication unit 109.

The communication unit 109 transmits the analysis target data provided from the preprocessing unit 107 to the analysis device 200. The analysis target data may be transmitted using, for example, wireless communication. The communication method is not particularly limited. However, for example, when the analysis device 200 is a server on a network, the Internet or the like can be used. When the analysis device 200 is located near the sensor device 100, for example, Bluetooth (registered trademark) or a wireless area network (LAN) may be used. Since (the analysis target data may not necessarily be transmitted in real time to the analysis device 200, for example, the analysis target data may be transmitted to the analysis device 200 through wired communication, for example, after a play ends.

(Analysis Device)

The analysis device 200 includes a communication unit 201, the preprocessing unit 203, and an analysis unit 205. The analysis device 200 may further include a storage unit 209 and an output unit 211. A hardware configuration realizing such functions will be described later.

The communication unit 201 receives the analysis target data transmitted from the sensor device 100. As described regarding the sensor device 100, the analysis target data can be transmitted using, for example, network communication such as the Internet, wireless communication such as Bluetooth (registered trademark) or wireless LAN, or wired communication. The communication unit 201 provides the received sensor information to the preprocessing unit 203. As will be described later, when the preprocessing unit 203 is not installed, the sensor information may be provided directly to die analysis unit 205.

The preprocessing unit 203 performs preprocessing on the data received by the communication unit 201. For example, the preprocessing unit 203 can function as the above-described segment setting unit. When the preprocessing unit 203 functions as the segment setting unit, the preprocessing unit 203 sets an analysis target segment (motion segment) in the same second time-series data (data obtained by the motion sensor 105 of the sensor device 100) received by the communication unit 201 based on the first time-series data (data obtained from the shock sensor 103 of the sensor device 100) received by the communication unit 201. The preprocessing unit 203 may provide only the second time-series data in the set analysis target segment to the analysis unit 205. Alternatively, the preprocessing unit 203 may generate separate data for indicating the set analysis target segment using a time stamp or the like of the time-series data and provide the separate data together with the second time-series data to the analysis unit 205.

When the preprocessing unit 107 of the sensor device 100 functions as the segment setting unit, the preprocessing in the analysis device 200 is not necessary, and thus the preprocessing unit 203 is not installed in some cases. Alternatively, the preprocessing unit 203 not only functions as the segment setting unit, but may also perform a process such as amplification of data or filtering of data equal to or less than a threshold value in place of the preprocessing unit 107 of the sensor device 100.

The analysis unit 205 performs analysis based on the second time-series data (data obtained from the motion sensor 105 of the sensor device 100) in the analysis target segment set by the segment setting unit (the preprocessing unit 107 or 203) and includes a motion pattern determination unit 207 that determines a motion pattern of a user. The motion pattern determination unit 207 may determine a motion pattern using the first time-series data (data obtained from the shock sensor 103 of the sensor device 100) in addition to the second time-series data. The analysis unit 205 may further have a function of analyzing a play of a user based on data provided from the sensor device 100 in addition to the motion pattern determination unit 207. The analysis unit 205 may store the analysis result in the storage unit 209.

The output unit 211 is installed as necessary. In the example illustrated in FIG. 1, the analysts device 200 is realized as a server. Therefore, for example, the analysis result of the analysis unit 205 including information regarding a motion pattern of a user is transmitted from the communication unit 201 to a terminal device and is output from the terminal device. On the other hand, when at least some of the functions of the analysis device 200 are realized by a terminal device such as a smartphone, a tablet terminal, or various PCs, the output unit 211 that outputs the analysis result is installed in the analysis device 200 to output the analysis result as an image or audio. When the analyst result is displayed as an image, the image may include an image or text indicating a motion pattern of a user. An example of information output from the output unit 211 will be described later.

(3. Processing Flow)

Next, an example of a process according to the embodiment of the present technology will be described in comparison with a reference example with reference to FIGS. 5 to 8.

Figure 5:
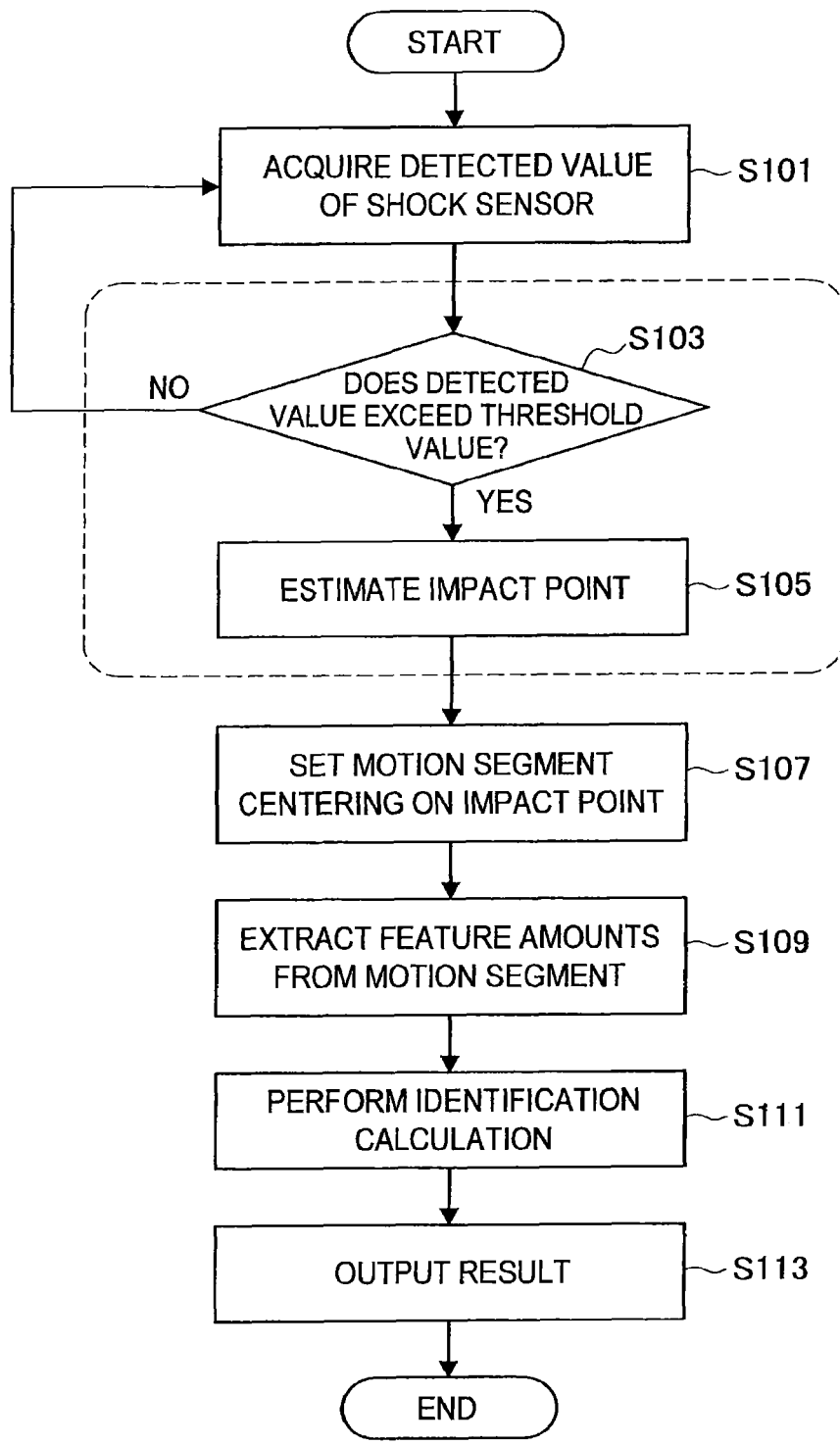
FIG. 5 is a flowchart illustrating an example of a process according to an embodiment of the present technology.

FIG. 5 is a flowchart illustrating an example of the process according to the embodiment of the present technology. Referring to FIG. 5, the preprocessing unit 203 (or the preprocessing unit 107 of the sensor device 100; can be interpreted as the preprocessing unit 107 although only the preprocessing unit 203 is described representatively below in some cases) of the analysis device 200 acquires a detected value of the shock sensor 103 from the first time-series data (step S101).

Next, the preprocessing unit 203 determines Whether the detected value acquired in step S101 exceeds a predetermined threshold value (step S103). Here, when the detected value exceeds the threshold value (YES), the preprocessing unit 203 estimates that this time point is an impact point (step S105) and allows the process to proceed to a motion identification process to be described below. Conversely, when the detected value does not exceed the threshold value in step S103 (NO), the preprocessing unit 203 acquires a detected value of the shock sensor 103 in a subsequent time window without performing the motion identification process any longer (step S101).

When the impact point is estimated in step S105, the preprocessing unit 203 sets a motion segment centering on the impact point. For example, the length of the motion segment before and after the impact point can be set using the longest motion segment as a criterion in each identifiable motion pattern. For example, in the example of tennis, when a motion pattern in which a feature motion is shown earliest when viewed from the impact point is a backhand volley, the motion segment is set using the starting point (for example, the impact point 0.5 seconds prior) at the feature motion of the backhand volley as a starting point. Likewise, when a motion pattern in which a feature motion continues later when viewed from the impact point is a forehand slice, the motion segment is set using the ending point (for example, the impact point 1 second after) of the feature motion of the forehand slice as an ending point. That is, the length of the motion segment is set such that a feature motion of each motion pattern is included.

Next, the analysis unit 205 extracts feature amounts from the set motion segment (step S109). When the processes of step S101 to step S107 are performed by the preprocessing unit 107 of the sensor device 100, at least data of the motion segment is transmitted from the sensor device 100 to the analysis device 200 between step S107 and step S109. The features extracted in step S109 can be frequency features of a signal waveform or statistical features of a time waveform such as an average, a dispersion, a minimum value, and a maximum value, as described above. For example, sensor output waveforms it the times of a forehand stroke and a serve are illustrated in FIGS. 10A and 10B. When the sensor output waveforms are compared, different features are particularly shown in an amplitude of a time waveform such as ω-X or ω-Z. Before the extraction of the features, missing portions of signal waveforms may be interpolated. The extracted features may be subjected to a statistical process such as normalization.

Next, the analysis unit 205 performs identification calculation based on the feature amounts extracted in step S109 (step S111). As described above, referring to the identification dictionary prepared beforehand, the identification calculation can be performed, for example, using a non-rule based method of forming identification parameters from data by machine learning such as a neural network, an SVM, a k-neighborhood identifier, and Bayes' classification. Thereafter, the analysis unit 205 outputs a result of the identification calculation (step S113). The result of the identification calculation can be stored in the storage unit 209. Thereafter, the analysis result may be transmitted to a terminal device which the user uses via the communication unit or may be output from the self-output unit 211 of the analysis device 200.

In a modification example of this embodiment, the estimation of the impact point in step S103 and step S105 described above may be substituted with another step. For example, when time-series data of detected values of the shock sensor is subjected to a Fourier transform and a frequency feature including an eigenfrequency of the user or equipment on which the sensor device 100 is mounted is detected, an impact point may be estimated to be present in the segment and a motion segment may be set centering on the segment.

REFERENCE EXAMPLE

Figure 6:
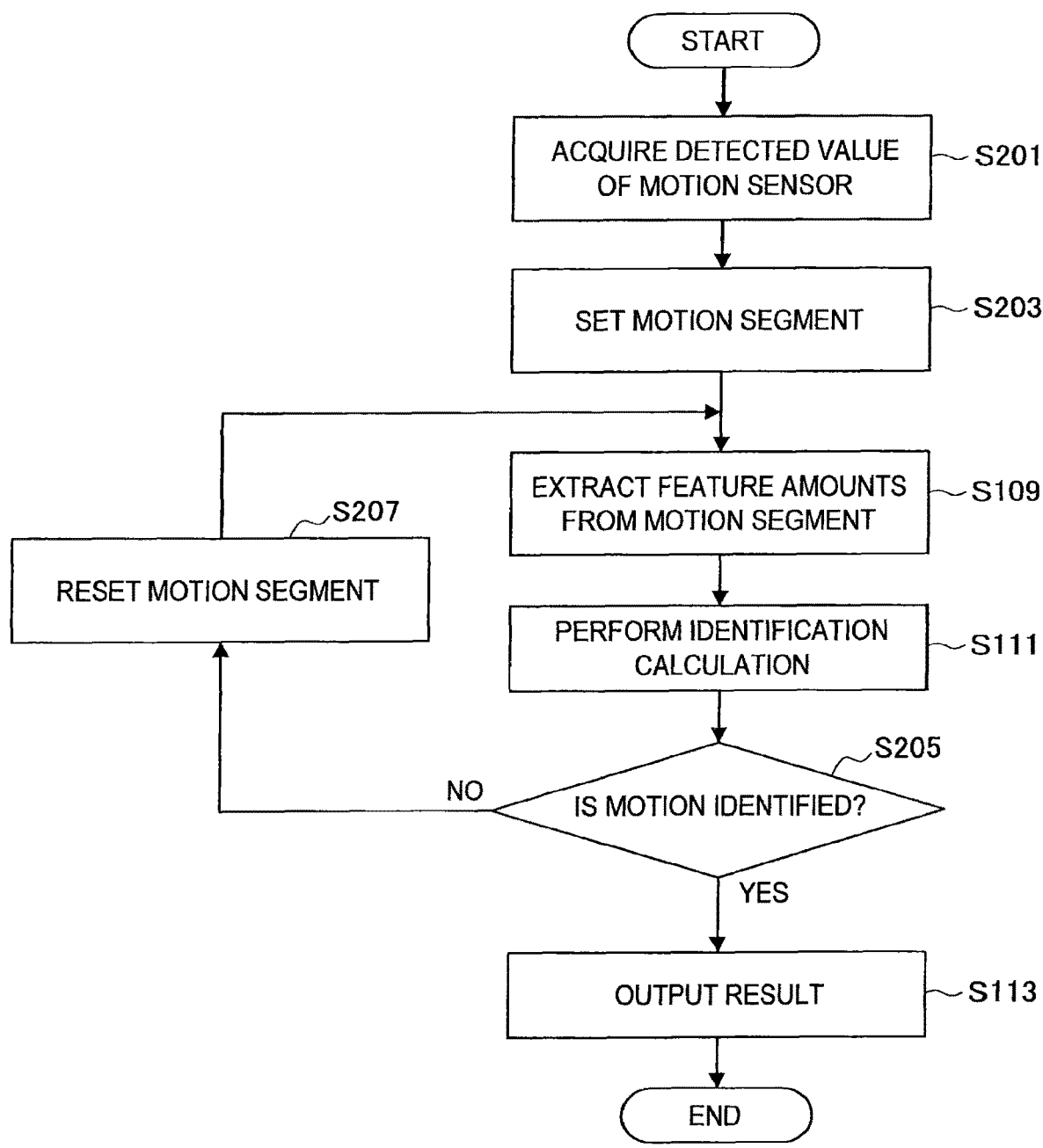
FIG. 6 is a flowchart illustrating a reference example of an example of FIG. 5.

FIG. 6 is a flowchart illustrating a reference example of the example of FIG. 5. In the example illustrated in FIG. 6, the detected value of the shock sensor 103 is not used for a process (the sensor device 100 does not include the shock sensor 103) and the setting of the motion segment in the preprocessing unit 203 (or the preprocessing unit 107) is nut performed.

In the example illustrated in the drawing, the analysts unit acquires a detected value of the motion sensor (step S201). In the reference example, the detected value of the motion sensor is provided as unique time-series data. Next, (the analysis unit sets a motion segment (step S203). Here, since no detected value of the shock sensor is provided unlike the example of FIG. 5, the analysis unit sets the motion segment without a clue. For example, the analysts unit sets motion segments in order from a starting point of time-series data obtained from the motion sensor. For example, the length of the motion segment can be set as in the example of FIG. 5.

Next, as in the example of FIG. 5, the analysts unit extracts the feature amounts from the motion segment (step S109) and further performs the identification calculation (step S111). However, since the motion segment in step S203 is set without a clue, the motion pattern may not be identified in identification calculation of step S111 in some cases. On the other hand, the motion segment does not correspond to an actual feature motion and the motion pattern is not identifiable in the identification calculation in many cases.

Thus, the analysis unit determines whether a motion is identified in the identification calculation (step S205). When the motion is identified (YES), the analysis unit outputs a result of the identification result as in the example of FIG. 5 (step S113). Conversely, when the motion is not identified in step S205 (NO), the analysis unit resets a motion segment (step S207). The motion segment is reset, for example, by offsetting the segment set in step S203 (or step S207 of the previous time) by a predetermined time. For the reset motion segment, the analysis process of step S109 and step S111 is performed again.

Figure 7:
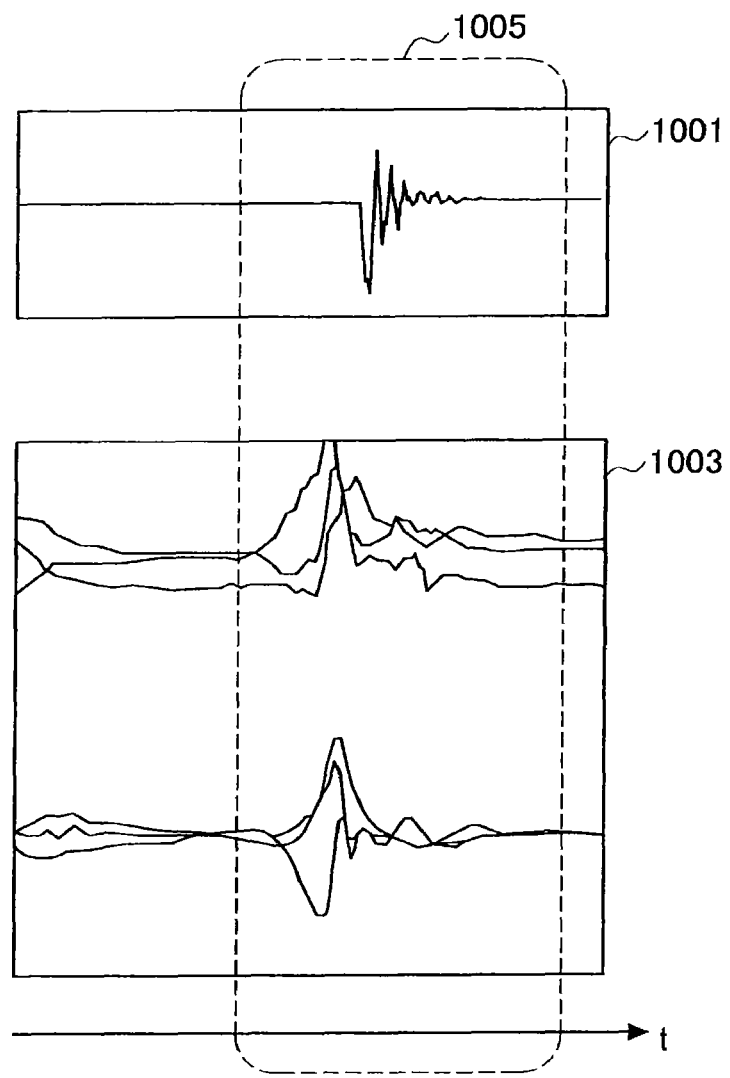
FIG. 7 is a diagram for describing setting of a motion segment in the example of FIG. 5.
Figure 8:
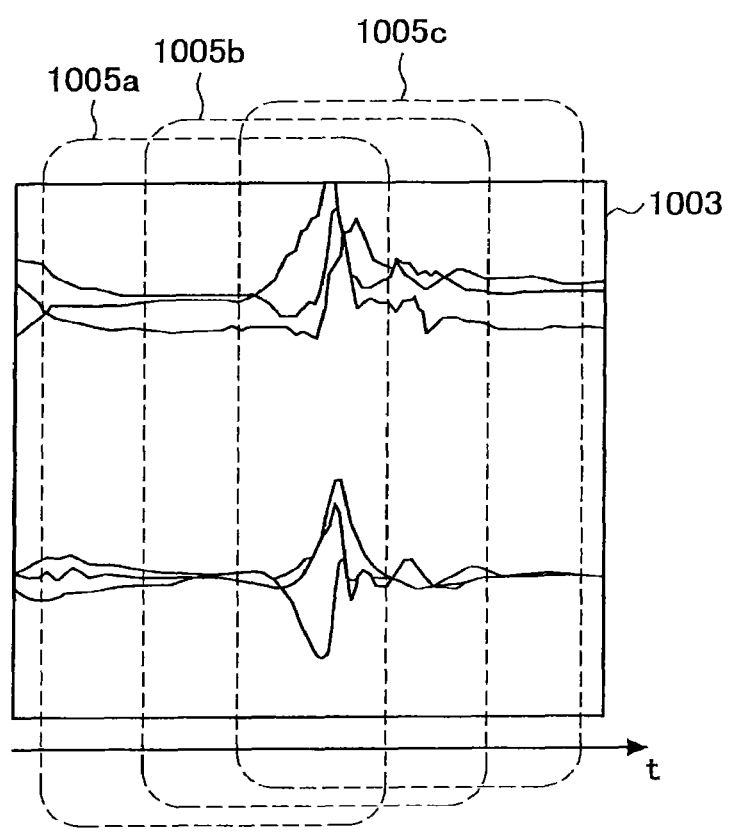
FIG. 8 is a diagram for describing setting of a motion segment of the example of FIG. 6.

FIGS. 7 and 8 are diagrams for describing the setting of the motion segment in the examples of FIGS. 5 and 6 described above. Hereinafter, the advantages of the process according to this embodiment in comparison of the reference example will be described with reference to these drawings.

In this embodiment, as illustrated in FIG. 7, a motion segment 1005 in time-series data 1003 of the motion sensor is set based on time-series data 1001 of the shock sensor. Accordingly, for example, a segment in which a feature motion such as hitting of a ball by equipment or the body of a user, stomping of a user on the surface of the ground, or a colliding action with another user is highly likely to occur can be set in the motion segment 1005 from the beginning.

On the other hand, in the reference example illustrated in FIG. 8, there is no clue for setting the motion segment 1005 in the time-series data 1003 of the motion sensor. Therefore, for example, the motion segment set by guess, as mentioned in step 8203 of FIG. 6, is repeatedly reset, as described in step S207, and thus a suitable motion segment is found. In the example illustrated in FIG. 8, motion segments 1005a, 1005b, and 1005c are sequentially set. When a feature amount in one of the motion segments indicates a feature "motion-like" and the motion is identified, the fact that the motion segment is the suitable motion segment is determined afterwards.

In both of the foregoing examples of FIGS. 7 and 8, the determination of the motion pattern itself can be made. In the reference example illustrated in FIG. 8, however, from a statistical viewpoint, it is necessary to repeat the identification calculation in the motion segment set by guessing several times in order to suitably set one motion segment. Accordingly, die calculation cost necessary for the determination of the motion pattern may be high. Further, when offset widths (offset widths of the segment 1005a→the segment 1005b and the segment 1005b→the segment 1005c illustrated in the example of FIG. 8) at the lime of the update of the motion segment arc set to be large to suppress the calculation cost, for example, there is a probability of the set motion segment temporally passing the suitable motion segment, thereby deteriorating accuracy of the determination of the motion pattern.

On the other hand, in the example of this embodiment illustrated in FIG. 7, the suitable motion segment can lie set from the beginning. Therefore, the calculation cost can be suppressed without deterioration in (the accuracy of the determination of the motion pattern. In the example of this embodiment, however, as described in FIG. 7, the motion segment is set based on the time-series data 1003 of the shock sensor. Therefore, it is difficult to apply the setting of the motion segment to a motion occurring without a shock, detected by the shock sensor, for example, an air swing. When it is necessary to identify such a motion, the process as in the reference example illustrated in FIG. 8 can be used.

As described above, a dynamic range of the motion sensor with respect to a value of an acceleration is relatively small. Therefore, when a shock is applied to a user or equipment, the occurring acceleration is not accurately detected in many cases since the acceleration exceeds the dynamic range. Therefore, it is difficult to use the same sensor as both of the shock sensor and the motion sensor. Accordingly, in this embodiment, a shock is detected using a shock sensor which is a separate sensor and the detected shock is used to set a motion segment. When an acceleration occurring due to a shock is within the dynamic range of the motion sensor in consideration of the nature of a sport or performance of a sensor, the same sensor may be used as both of the shock sensor and the motion sensor.

(4. Specific Example)

Next, a specific example of sensor data according to the embodiment of the present technology will be described with reference to FIGS. 9, 10A, and 10B.

FIG. 9 is a graph illustrating a specific example of the sensor data according to the embodiment of the present technology. In FIG. 9, acceleration data (SHOCK) of the shock sensor, acceleration data (a-X, a-Y, and a-Z) of a triaxial acceleration sensor which is the motion sensor, and angular speed data ($\omega$-X, $\omega$-Y, and $\omega$-Z) of a triaxial gyro sensor which is the same motion sensor are shown in a time-series manner.

In this embodiment, as described above, the motion segment 1005 is set in the time-series data of the motion sensor based on the time-series data of the shock sensor. In this example, the shock sensor detects an acceleration of a high frequency occurring due to a shock applied to a user or equipment, whereas the shock sensor does not detect an acceleration of another low frequency or a stationary component. Accordingly; for example, when any change is shown in the time-series data of the shock sensor, the changed point can be regard as a shock occurring time point, that is, an impact point. In the example illustrated in the drawing, points before and after the point at which the change is shown in the time-series data of the shock sensor are automatically set as the motion segment 1005.

On the other hand, in a segment other than the motion segment 1005, a change is also shown in the acceleration data or the angular speed data of the motion sensor. For example, segments 1007a, 1007b, and 1007c shown in the drawing are not the motion segment. However, a change in an amplitude is shown to the same degree as the motion segment of the acceleration or the angular speed. For example, in the process of determining the motion pattern in the reference example in which the data of the shock sensor is not used, as illustrated in FIGS. 6 and 8 described above, these segments may be suspicious segments in which a specific motion occurs or does not occur. That is, although a specific motion actually occurs in the motion segment 1005, there is a probability of erroneous recognition that a motion also occurs in the segment 1007. In this embodiment, since the suspicious segments can be excluded from identification calculation targets under the condition in which a specific motion is accompanied with a shock, the calculation cost can be suppressed and the accuracy of the determination of the motion pattern can be improved.

FIGS. 10A and 10B are graphs illustrating specific examples of the sensor data according to the embodiment of the present technology. In FIGS. 10A and 10B, acceleration data (SHOCK) of the shock sensor, acceleration data (a-X, a-Y, and a-Z) of the triaxial acceleration sensor which is the motion sensor, and angular speed data ($\omega$-X, $\omega$-Y, and $\omega$-Z) of the triaxial gyro sensor which is the same motion sensor arc shown in a time-series manner, as in FIG. 9.

In FIGS. 10A and 10B, the case of a forehand stroke of tennis and the case of a serve of tennis are illustrated respectively as examples of the sensor data corresponding to the motion pattern. In both of the examples, feature waveforms are shown in the time-series data of the motion sensor, hut the motion segment 1005 set based on the time-series data of the shock sensor covers the feature waveforms. From the examples, it can be understood that the setting of the motion segment based on the data of the shock sensor according to this embodiment is effective for improvement of the accuracy of the determination of the motion pattern and suppression in the calculation cost.

(5. Example of Output Information)

Next, an example of information to be output according to the embodiment of the present technology will be described with reference to FIGS. 11 to 18. The information to be output according to this embodiment can include, for example, information indicating the motion pattern which is the analysis result of the analysis unit 205 of the analysis device 200, but various other kinds of information may be added. Since the added information can be generated appropriately using, for example, a technology of the related art the information to be output will be mainly described in the following, description and the detailed description of a method of generating the added information will be omitted.

In the following description, a screen displayed mainly in a display will be described, but the information to be output according to this embodiment of the present technology is not limited to an image or text displayed on a screen. For example, the information may be output as audio from a speaker, may be output as visual information other than an image by a lamp or the like, or may be output by vibration. As described above, for example, the information may out be output from an output unit of the self-analysis device 200 when the analysis device 200 is a terminal device. The information may be output from an output unit of a terminal device of a client connected to a server on a network when the analysis device 200 is the server on the network.

Figure 11:
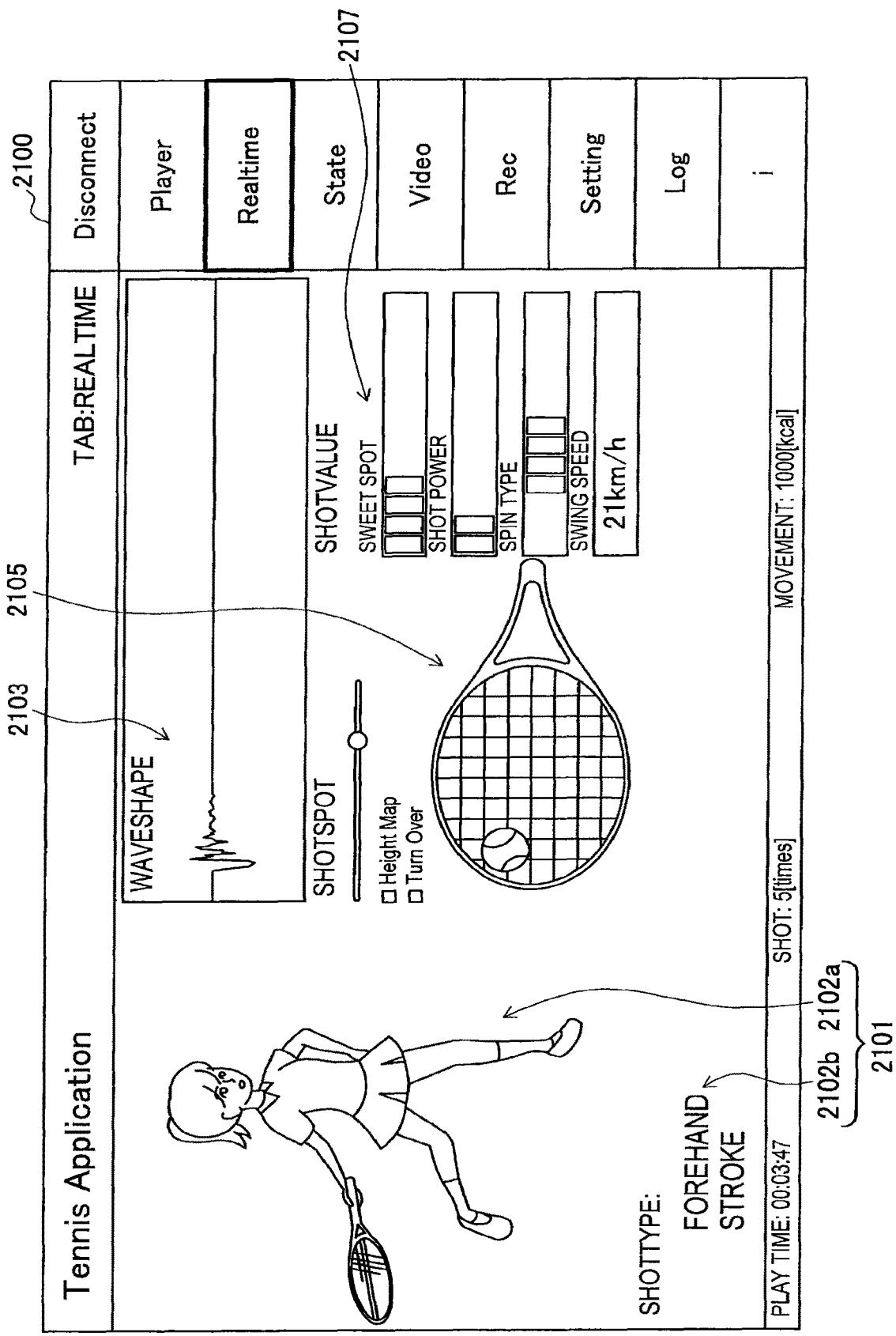
FIG. 11 is a diagram illustrating a first screen example according to an embodiment of the present technology.

FIG. 11 is a diagram illustrating a first screen example according to the embodiment of the present technology. Referring to FIG. 11, a screen 2100 includes a motion pattern display 2101, a waveform display 2103, an impact position display 2105, and a SHOT VALUE display 2107.

The motion pattern display 2101 displays a motion pattern (which is expressed as a SHOTTYPE in this screen) determined in the analysis device 200. In the example illustrated in the drawing, the fact that the determined motion pattern is a "forehand stroke" is displayed. The motion pattern display 2101 may include, for example, an icon 2102a and text 2102b showing the motion.

FIG. 12 is a diagram illustrating another example of the motion pattern display 2101. In FIG. 12, a motion pattern display 2101a of "SMASH", a motion pattern display 2101b of "BACKHAND STROKE," and a motion pattern display 2101c of "FOREHAND STROKE" are illustrated. Of course, the motion pattern display 2101 is not limited to these examples. For example, as exemplified in Table 1 above, numerous other motion patterns can be defined for the item "tennis" and motion patterns can be defined likewise for other items "baseball" and "soccer." The motion pattern display 2101 can be set for each of the motion patterns defined in this way.

Referring back to FIG. 11, for example, the waveform display 2103 displays a waveform of time-series data detected by the sensor 101 of the sensor device 100. For example, the waveform display 2103 may be displayed as one of the visual effects. In the example illustrated in the drawing, the waveform of the time-series data by the shock sensor is displayed as the waveform display 2103. However, the waveform of the time data by the motion sensor may be likewise displayed or both waveforms thereof may be displayed.

The impact position display 2105 displays a position (impact position) which is specified by a process separate from the determination of the motion pattern and at which a ball hits a racket. Like the example illustrated in the drawing, when a motion pattern is an action (shot) of hitting a ball, the user can comprehend the impact position due to the display of the impact position display 2105. For example, it is possible to obtain information indicating whether the impact position is an intended position or is deviated from an exemplary position. The object hitting the ball need not be an instrument, but may also be part of a user's body, such as the user's arm or hand (e.g., playing handball). Other instruments for other sports, such as baseball bats, and golf clubs may be used as well.

Figure 13:
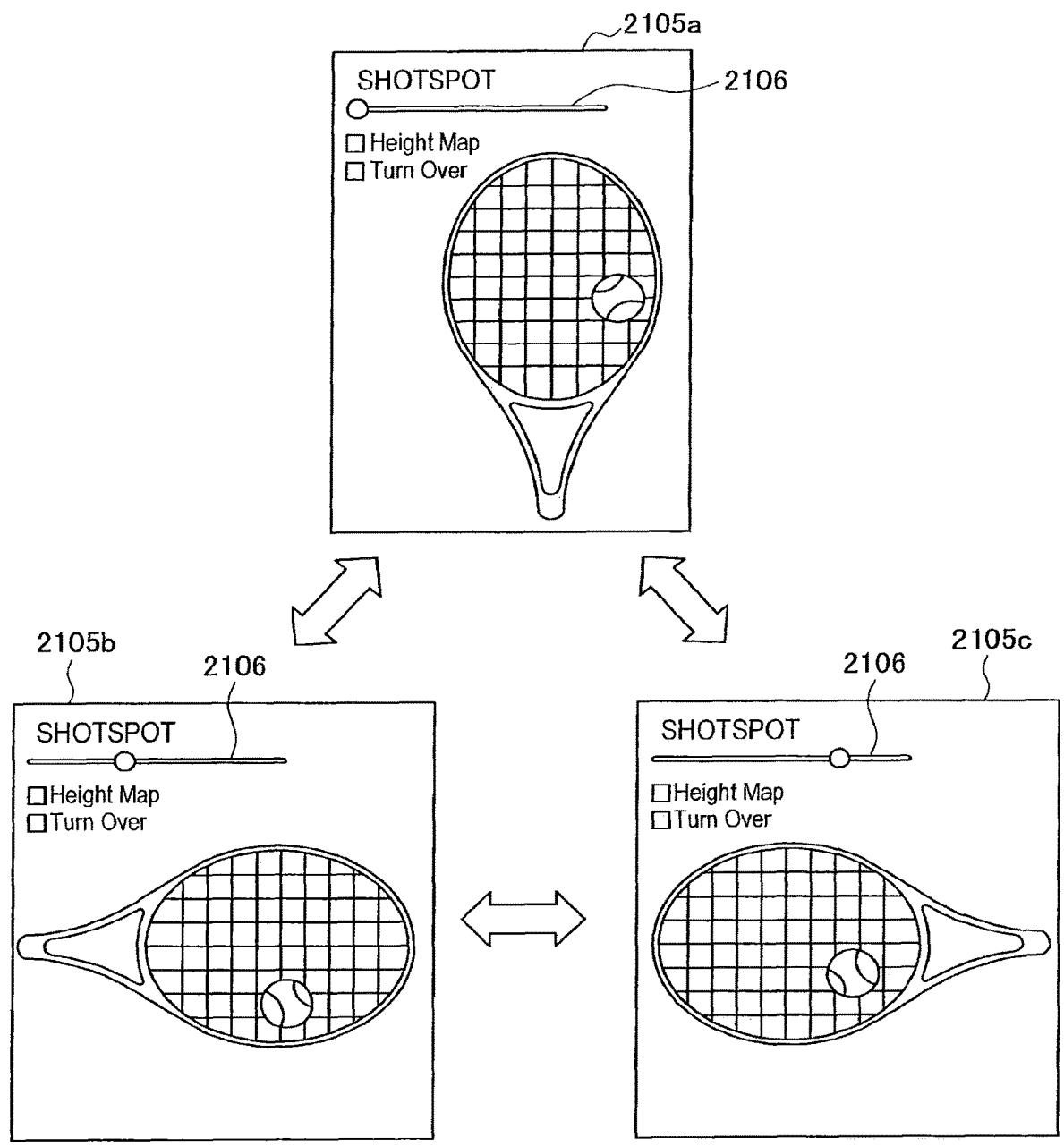
FIG. 13 is a diagram illustrating examples in which impact position displays are changed according to motion patterns according to an embodiment of the present technology.

FIG. 13 is a diagram illustrating an example in which the impact position display 2105 is changed according to a motion pattern. In FIG. 13, an impact position display 2105a when the motion pattern is a "SMASH," an impact position display 2105b when the motion pattern is a "BACKHAND STROKE," and an impact position display 2105c when the motion pattern is a "FOREHAND STROKE" are illustrated. As in the example, a direction (a rotation angle in a planar direction) of a racket displayed at the impact position display 2105 may differ according to the motion pattern. By displaying the racket of the impact position display 2105 in a direction close to the actual direction of the racket in the case of each motion pattern, the user can comprehend the impact position of the ball more intuitively. By operating a slider 2106, the user can freely change the direction of the racket.

Figure 14:
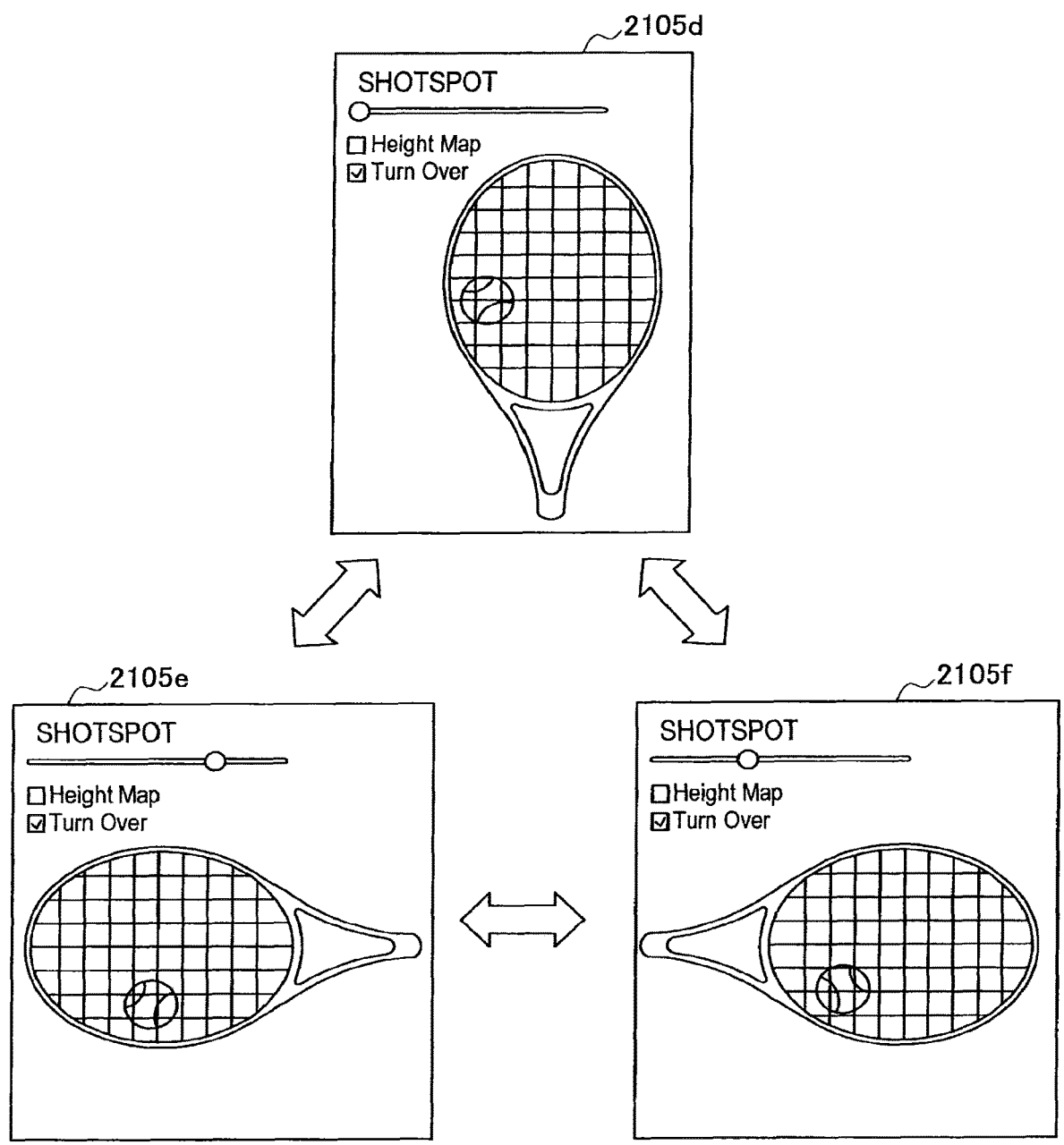
FIG. 14 is a diagram illustrating display examples when the impact position displays are reversed according to an embodiment of the present technology.

FIG. 14 is a diagram illustrating a display example when a check box labeled "Turn Over" included in the impact position display 2105 is checked. In this case, the front and back of the racket are reversed and displayed at the impact position display 2105. In the example:illustrated in the drawing, an impact position display 2105d when the motion pattern is a "SMASH," an impact position display 2105e when the motion pattern is a "BACKHAND STROKE," and an impact position display 2105f when the motion pattern is a "FOREHAND STROKE" are illustrated. In all of the displays, the front and back of the racket are reversed by rotating the racket 180° using a shaft as an axis, in comparison to each impact position display 2105 illustrated in FIG. 13.

Referring back to FIG. 11, the SHOTVALUE display 2107 displays various index values regarding the motion pattern (here, a shot) specified through a process separate from the determination of the motion pattern. In the example illustrated in the drawing, a sweet spot hit probability, a shot power, a spin type, and a swing speed are displayed, but other index values may be displayed.

Figure 15:
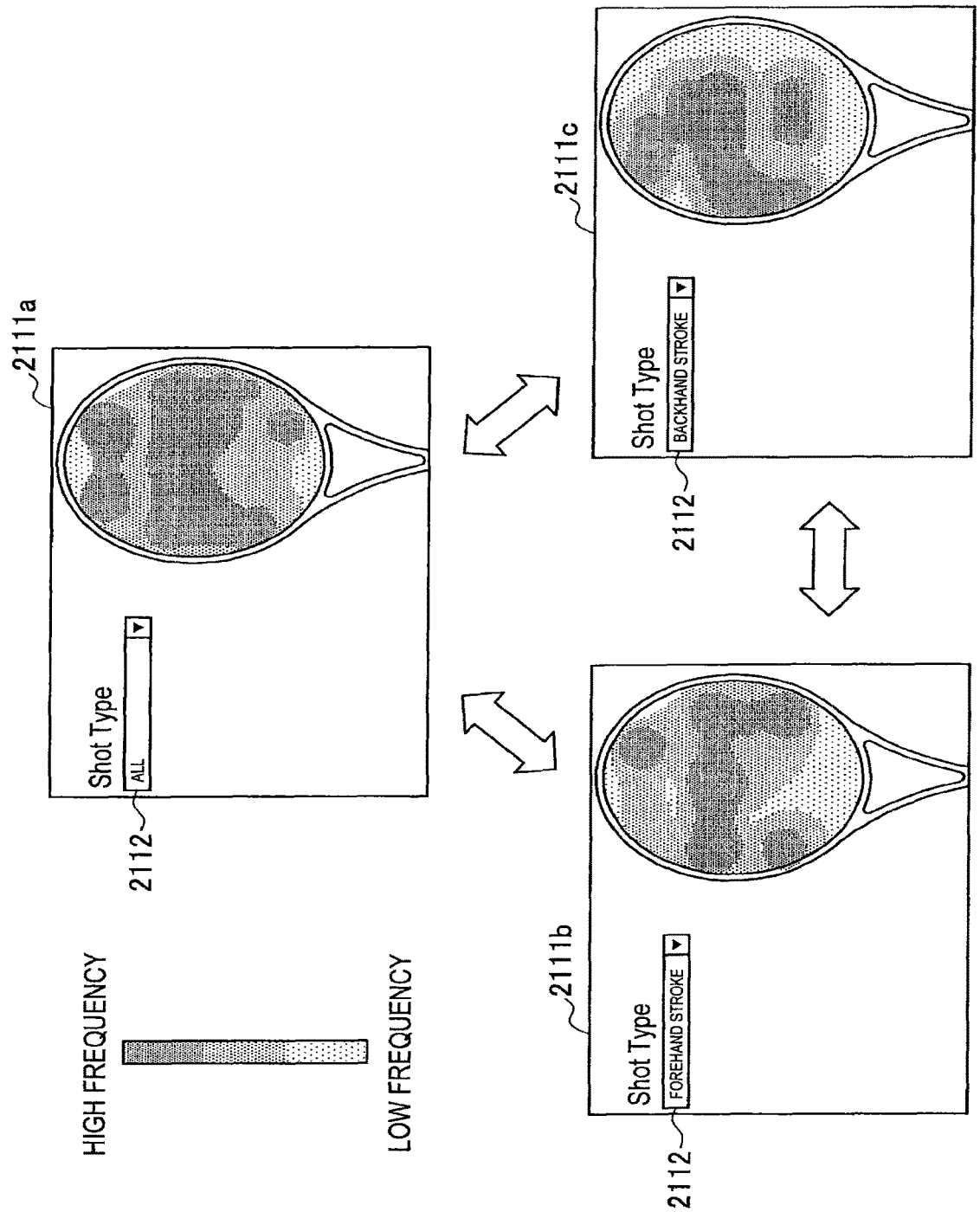
FIG. 15 is a diagram illustrating examples of impact position distribution displays according to an embodiment of the present technology.

FIG. 15 is a diagram illustrating an example of an impact position distribution display 2111 as another display example. The impact position distribution display 2111 shows a statistical distribution of the impact positions specified together with the motion patterns (in the foregoing example, the smash, the backhand stroke, the forehand stroke, and the like) of the shot. A collection target can be changed with shot type selection 2112. For example, in an impact position distribution display 2111a, "ALL" is selected with the shot type selection 2112 and a distribution of the impact positions collected for all shot types is displayed. Further, for example, a distribution of the impact positions may be displayed according to color classification for each frequency, as illustrated in the drawing.

On the other hand, in the impact position distribution display 211b, the "FOREHAND STROKE" is selected with the shot type selection 2112 and a distribution of the impact positions collected when the shot type (which can be determined as the motion pattern) is the "FOREHAND STROKE" is displayed. Further, in the impact position distribution display 2111c, the "BACKHAND STROKE" is selected with the shot type selection 2112 and a distribution of the impact positions collected when the shot type is the "BACKHAND STROKE" is displayed. With the displays, the user can intuitively recognize the distribution of the impact positions for each shot type. For example, when a tendency for the impact position to deviate: from the intended position or an exemplary position is shown, the user can perform a play while being conscious of correction of the impact position.

Figure 16:
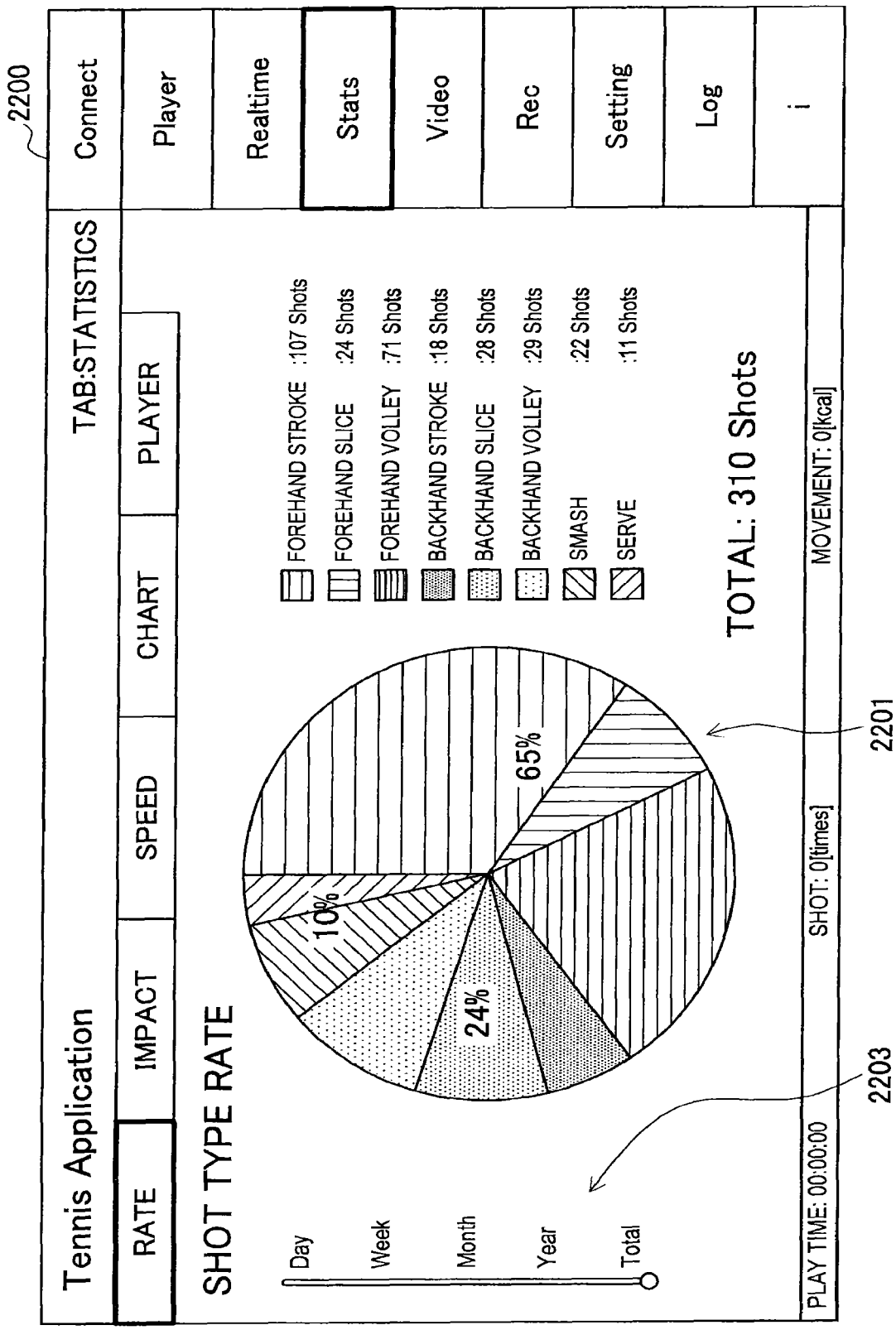
FIG. 16 is a diagram illustrating a second screen example according to an embodiment of the present technology.

FIG. 16 is a diagram illustrating a second screen example according to the embodiment of the present technology. Referring to FIG. 16, a screen 2200 includes a shot type ratio display 2201. In this embodiment, since shot types (types of swings) can be determined through the determination of the motion pattern, not only simple impact counters (the number of shots or swings is counted) but also detailed statements of the shots or the swings can be displayed by the shot type ratio display 2201. By operating a slider 2203, target periods of the shot type ratio display 2201 can be selected from the past day, week, month, or year from the very beginning, and the like.

Figure 17:
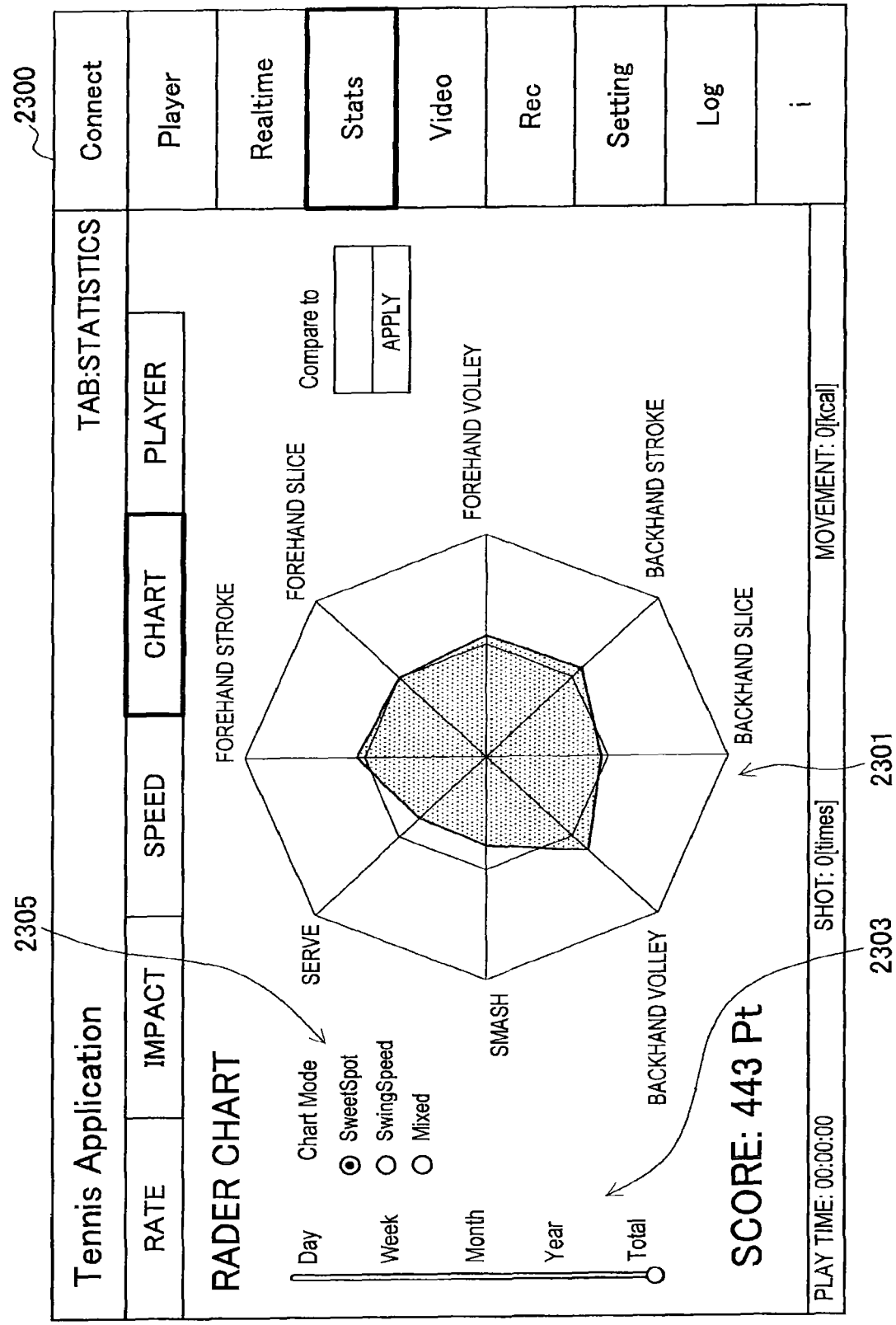
FIG. 17 is a diagram illustrating a third screen example according to an embodiment of the present technology.

FIG. 17 is a diagram illustrating a third screen example according to the embodiment of the present technology. Referring to FIG. 17, a screen 2300 includes a score chart display 2301. In this embodiment, since shot types (types of swings) can be determined through the determination of the motion pattern and information such as an impact position or the like for each shot can be acquired, as illustrated in the example of FIG. 11 or the like, a score can be calculated for each shot type and can be displayed as the score chart display 2301. As in the example of FIG. 16 described above, by operating a slider 2303, target periods of the score chart display 2301 can be selected from the past day, week, month, or year, from the very beginning, and the like.

In the example illustrated in the drawing, a score type selection 2305 is also displayed. The score type selection 2305 is a display for selecting a score type displayed as the score chart display 2301 among three score types, i.e., a SweetSpot, SwingSpeed, and Mixed. Further, a sweet spot score is a score indicating how close an impact position for each shot is to a so-called sweet spot. A higher score indicates that the user hits a ball in a sweet spot more accurately at the time of the shot.

Figure 18:
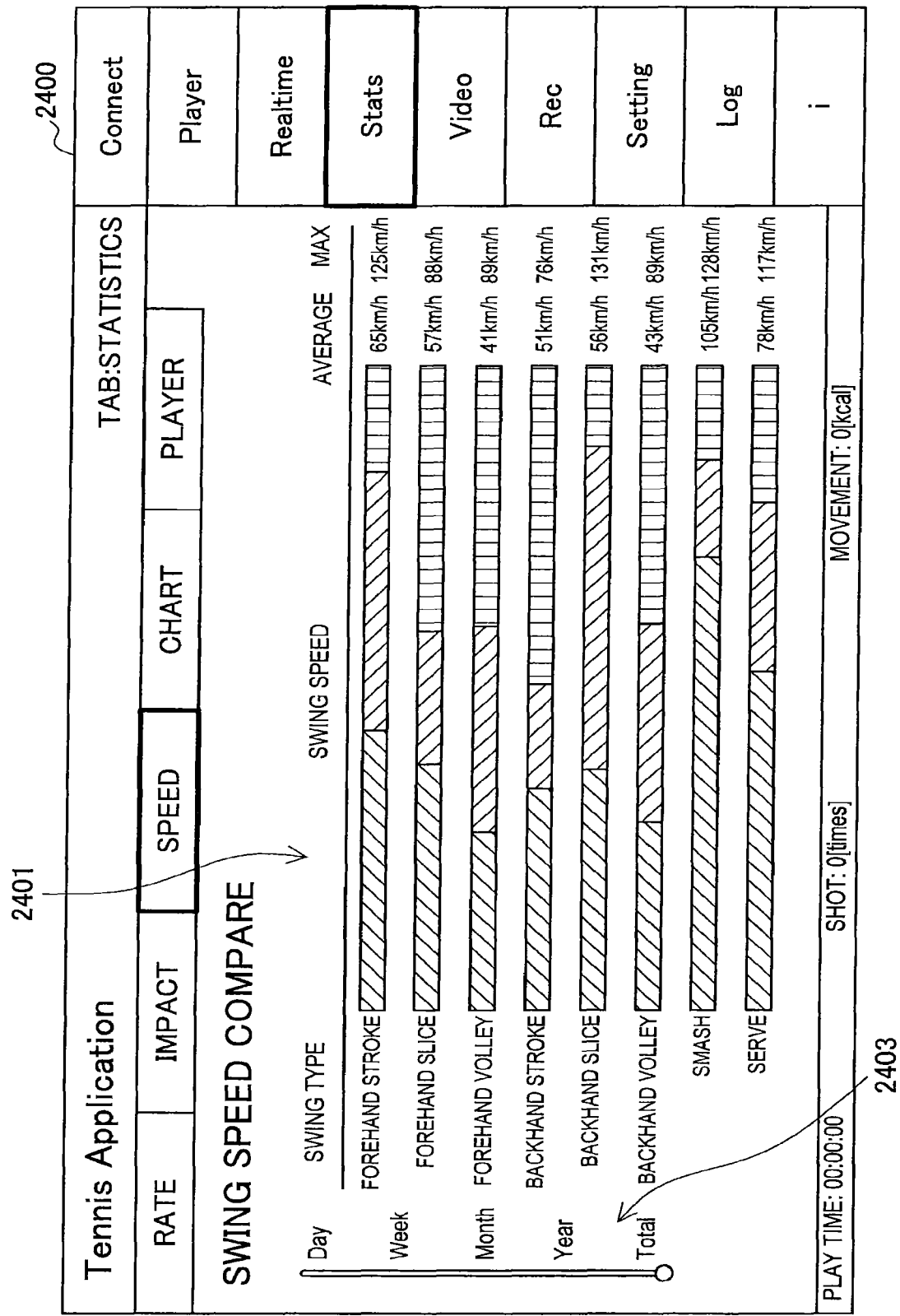
FIG. 18 is a diagram illustrating a fourth screen example according to an embodiment of the present technology.

FIG. 18 is a diagram illustrating a fourth screen example according to the embodiment of the present technology. Referring to FIG. 18, a screen 2400 includes a swing speed graph display 2401. In this embodiment, since shot types (types of swings) can be determined though the determination of the motion pattern and information such as a swing speed for each shot can be acquired, as illustrated in the example of FIG. 11 or the like, the swing speed can be collected for each shot type and can be displayed together with an average value or a maximum value as the graph. As in the examples of FIGS. 16 and 17 described above, by operating a slider 2403, target periods of the swing speed graph display 2401 can be selected from the past day, week, month, or year, from the very beginning, and the like.

(6. Hardware Configuration)

Next, examples of hardware configurations for realizing a sensor device and an analysis device according to embodiments of the present technology will be described with reference to FIGS. 19 and 20.

(Sensor Device)

Figure 19:
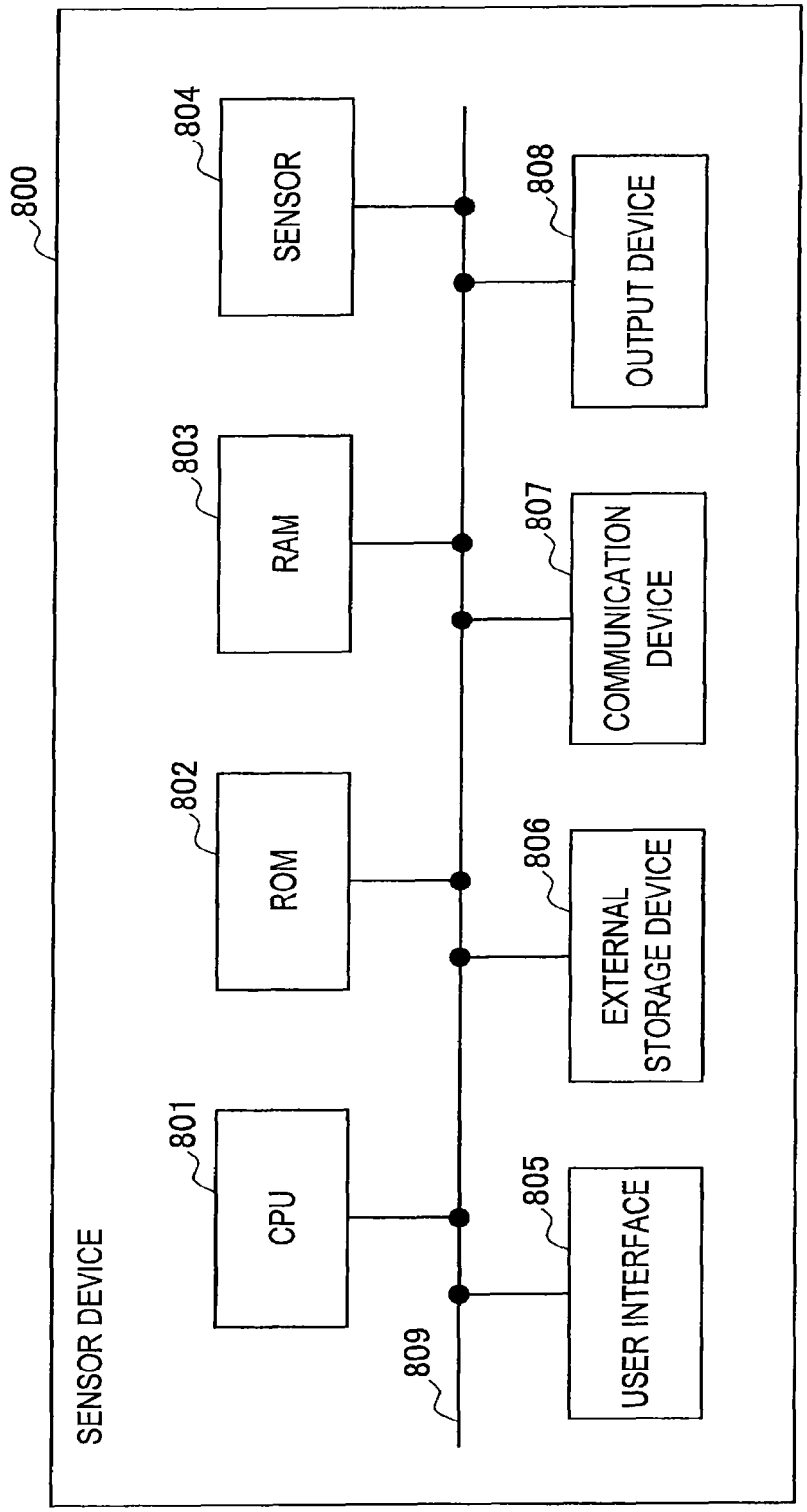
FIG. 19 is a diagram illustrating an example of a hardware configuration of a sensor device according to an embodiment of the present technology.

FIG. 19 is a diagram illustrating an example of a hardware configuration of a sensor device according to an embodiment of the present technology. For example, a sensor device 800 can be realized as the sensor device 100 according to the foregoing embodiment.

The sensor device 800 includes a central processing unit (CPU) 801, a read-only memory (ROM) 802, a random access memory (RAM) 803, a sensor 804, a user interface 805, an external storage device 806, a communication device 807, and an output device 808. These constituent elements are connected to each other via, for example, a bus 809.

The CPU 801, the ROM 802, and the RAM 803 realize various functions in a software manner, for example, by reading and executing program commands recorded on the external storage device 806. In the embodiment of the present technology, for example, control of the entire sensor device 800 or the functions of the preprocessing unit 107 descried in the foregoing examples can be realized by the CPU 801, the ROM 802, and the RAM 803.

The sensor 804 corresponds to the sensor 101 in the functional configuration of the foregoing embodiment. The sensor 804 can include, for example, an acceleration sensor, an angular speed sensor, a vibration sensor, a temperature sensor, or a GPS receiver.

The user interface 805 receives a user's operation on the sensor device 800 and can be, for example, an input device such as a button or a touch panel. The user's operation is, for example, an operation instructing start or end of transmission of sensor information from the sensor device.

The external storage device 806 stores various kinds of information regarding the sensor device 800. For example, the external storage device 806 may store program commands causing the CPU 801, the ROM 802, and the RAM 803 to realize the functions in a software manner or may temporarily cache data acquired by the sensor 804. When the sensor device 800 is considered to be mounted on the user himself or herself or sporting equipment, for example, a storage device such as a semiconductor memory that is strong against shock is used as the external storage device 806.

The communication device 807 corresponds to the communication unit 109 in the functional configuration of the foregoing embodiment. The communication device 807 communicates with an analysis device 900 to be described below in conformity with various wired or wireless communication schemes. The communication device 807 may communicate directly with the analysis device 900 through inter-device communication or may communicate with the analysis device 900 via a network such as the Internet.

The output device 808 is configured as a device that can visually or audibly notify a user of the acquired information. The output device 808 can be, for example, a display device such as a liquid crystal display (LCD) or an audio output device such as a speaker or a headphone. Although not described in the foregoing embodiment, when information indicating an analysis result such as a motion pattern is fed back from the analysis device to the sensor device, for example, in another embodiment, the information can be output from the output device 808. The sensor device 800 may further include a lighting unit such as an LED lamp or a vibrator that provides vibration to a user or equipment as an output unit.

(Analysis Device)

FIG. 20 is a diagram illustrating art example of a hardware configuration of an analysis device according to an embodiment of the present technology. For example, an analysis device 900 can ho realized as the analysis device 200 according to the foregoing embodiment.

The analysis device 900 can include a CPU 901, a ROM 902, a RAM 903, a user interface 905, an external storage device 906, a communication device 907, and an output device 908. These constituent elements arc connected to each other via, for example, a bus 909.

The CPU 901, the RUM 902, a id the RAM 903 realize various functions in a software manner, for example, by reading and executing program commands recorded on the external storage device 906. In the embodiment of the present technology, for example, control of the entire analysis device 900 or the functions of the preprocessing unit 203 and the analysis unit 205 described in the foregoing examples can lie realized by the CPU 901, the ROM 902, and the RAM 903.

The user interface 905 receives a user's operation on the analysis device 900 and can be, for example, an input device such as a button or a touch panel.

The external storage device 906 stores various kinds of information regarding the analysis device 900. For example, the external storage device 906 may store program commands causing the CPU 901, the ROM 902, and the RAM 903 to realize the functions in a software manner or may temporarily cache sensor information received by the communication device 907. The external storage device 906 may function as the storage unit 209 described in the foregoing example and store logs such as the sensor information or the determination result of the motion pattern.

The output device 908 is configured as a device that can visually or audibly notify a user of information. The output device 908 can be, for example, a display device such as an LCD or an audio output device such as a speaker or a headphone. When the analysis device 900 is a terminal device used by the user, the output device 908 causes the display device to display a result obtained through a process of the analysis device 900 as text or an image or allows a speaker or the like to output the result as audio.

The analysis device 900 may be implemented in a wearable computer device, such as a watch-type device, smartwatch, head mounted display device, glass-type device, ring-type device for finger or smartglasses. Also, while much of the description has been directed to a tennis example, the target segments of other motion patterns may be used as well, such as a baseball swing (the shock event occurs when the baseball hits the baseball bat, and the user moves the baseball bat in certain motions based on the type of pitch). Similarly, the shock sensor and motion sensor may be attached to a shaft of a golf club and the shock event occurs when the club strikes the golf ball.

The sensors communicate wirelessiy with the wearable computer device so that the type of shot, impact statistics, swing indices (2107 in FIG. 11), etc. may be shown in the displays of the wearable computer devices. In this way, the user can view on his smartwatch, where the golf ball was struck on the clubface, whether the swing was on plane, or inside/out, or outside/in, etc. Furthermore, the smart watch could keep track of the number of strokes by counting the number of impact events with the golf ball. Each club could be equipped with sensors, or the user's glove (or smartwatch) could be equipped with the sensors and detect the impact event through conduction of the shock event through the user's skeletal structure.

(7. Supplement)

In the foregoing embodiment, die information processing system including the sensor device and the analysis device (both of which can be information processing devices) has been described. In an embodiment of the present technology; the information processing system further includes for example, a server (includes a device realized as a collective of functions of a plurality of devices) on a network which realizes at least some of the functions of the analysts device, a program causing a computer to realize the functions of the device, and a storage medium which records the program and is a non-temporary tangible medium.

In the foregoing embodiment, the example in which one sensor device is used has been described. However, in an embodiment of the present technology, a plurality of sensor devices may be used. For example, in the case of tennis, a sensor device can be mounted on a racket which a user holds and other sensor devices may be mounted on shoes which the user wears. By combining and analyzing data provided from these sensor devices, a notion pattern of a higher-level such as a dash, a jump, a swing during forward movement, or a swing during backward movement can be determined. Even in this case, time-series data of a shock sensor of each sensor device can be used to specify a motion segment in time-series data of a motion sensor provided from each sensor device. When time-series data of motion sensors of sensor devices are synchronized, motion segments in the time-series data of the motion sensors of all of the sensor devices may be specified using the time-series data of one of the shock sensors of the devices. Alternatively, when each sensor device includes a shock sensor, time-series data of the motion sensor of each sensor device may be synchronized using the time-series data of the shock sensor.

In the foregoing embodiment, the example in which a motion pattern of one user is determined has been described. However, in an embodiment of the present technology, the number of users who arc motion pattern determination targets may be plural. For example, the analysis device may receive sensor information from each of the sensor devices of a plurality of users and may determine a motion pattern of each user. Information including the motion patterns determined by the separate analysis devices for the plurality of users may be shared via a network and, for example, information obtained by comparing the users in the information shown in the example of the foregoing screen can be provided.

In the foregoing embodiment, the example in which the sensor device and the analysis device are separate devices has been described. In an embodiment of the present technology, the sensor device and the analysis device may be integrated. In this case, the sensor device can acquire time-series data from a sensor, set a motion segment in the time-series data, determine a motion pattern through analysis of the motion segment, and output a determination result itself or transmit the determination to a server on a network or a terminal device.

The preferred embodiments of the present technology have been described in detail with reference to the appended drawings, but the technical range of the present technology is not limited to the examples.

Additionally, the present technology may also be configured as below.

(1) An information processing system comprising: processing circuitry configured to receive input data from a shock sensor which is configured to output data based on a shock on the shock sensor, and identify a target segment of time-series data that is output from a motion sensor that senses a motion of on object, wherein the target segment includes a pre-shock portion that occurs before a shock event and a post-shock portion that occurs after the shock event, the shock event is recognized based on the data from the shock sensor.

(2) the information processing system of (1), wherein the target segment is identified based on the data from the shock sensor.

(3) The information processing system of (1) or (2), wherein the shock event comprises an impact event including an impact on an object caused by a movement of a user.

(4) The information processing system of any of (1) to (3), wherein the object is an object held by the user, and the impact event includes a collision by the object and another object.

(5) The information processing system of any of (1) to (4), wherein the another object is one of a tennis ball, a golf ball, and a baseball.

(6) The information processing system of any of (1) to (5), wherein the object is a part of a body of the user.

(7) The information processing system of any of (1) to (6), wherein the shock sensor and the motion sensor are acceleration sensors.

(8) The information processing system of any of (1) to (7), wherein the system includes the shock sensor, the shock sensor having a greater dynamic range in acceleration than the motion sensor.

(9) The information processing system of any of (1) to (8), wherein the system includes the motion sensor, the motion sensor having a greater resolution of acceleration than the shock sensor.

(10) The information processing system of any of (1) to (9), wherein the motion sensor being configured to detect triaxial acceleration and angular speed.

(11) The information processing system of any of (1) to (10), wherein the processing circuitry is configured to analyze the target segment and identify a predetermined motion pattern of the object that corresponds with the target segment.

(12) The information processing system of any of (1) to (11), wherein the processing circuitry includes an output device that notifies a user of the predetermined motion pattern by generating at least one of an audio signal and a video signal.

(13) The information processing system of any of (1) to (12), further comprising: a display configured to display an indication of the predetermined motion pattern.

(14) The information processing system of any of (1) to (13), further comprising: a display configured to display an indication of an impact position of another object on the object.

(15) The information processing system of any of (1) to (14), further comprising: a display configured to display at least one index value associated with an actual motion pattern of the object.

(16) The information processing system of any of (1) to (15), further comprising: a display configured to display statistical feedback to a user regarding a plurality of detected movement patterns of the object.

(17) The information processing system of any of (1) to (16), wherein the motion sensor transmits the time-series data to the processing circuitry wirelessly.

(18) The information processing system of any of (1) to (17), wherein the processing circuitry is configured to identify the target segment by determining when the input data from the shock sensor exceeds a predetermined threshold, and a frequency of a signal described by the input data from the shock sensor.

(19) The information processing system of any of (1) to (18), wherein the information processing system is embodied in a watch-type device, and the processing circuitry is configured by a downloadable software application to identify the target segment.

(20) An information processing method comprising: receiving input data from a shock sensor which outputs data based on a shock on the shock sensor; receiving time-series data from a motion sensor that senses motion of an object; and identifying with processing circuitry a target segment of the time-series data, wherein the target segment includes a pre-shock portion that occurs before a Shock event and a post-shock portion that occurs after the shock event, the shock event is recognized based on the data from the shock sensor.

(21) A non-transitory computer readable storage device including instructions that when executed by a processor configure the processor to implement an information processing method, the method comprising: receiving input data from a shock sensor which outputs data based on a shock an the shock sensor; receiving time-series data from a motion sensor that senses motion of an object; and identifying with processing circuitry a target segment of the time-series data, wherein the target segment includes a pro-shock portion that occurs before a shock event and a post-shock portion that occurs after the shock event, the shock event is recognized based on the data from the shock sensor.

(22) An information processing device including: a sensor data acquisition unit that acquires first time-series data including a detected value of a first sensor detecting a shock transferred torr sensor device mounted directly or indirectly on a user who plays sports and second time-series data including a detected value of a second sensor detecting a physical behavior of the sensor device with a resolution higher than a resolution of the first sensor; and a segment setting unit that sets an analysis target segment in which analysis is performed to determine a motion pattern of the user in the second time-series data based on the first time-series data.

(23) The information processing device of (22), wherein the segment setting unit sets the analysis target segment using, as a reference, a point at which the detected value of the first sensor exceeds a predetermined threshold value.

(24) The information processing device of (23), wherein the segment setting unit sets the analysis target segment using, as a reference, a segment in which a frequency component of the detected value of the fact sensor includes an eigenfrequency of a mounted object of the sensor device.

(25) The information processing device of any one of (22) to (24), further including: an analysis unit that determines the motion pattern of the user based on the second time-series data in the analysis target segment.

(26) The information processing device of any one of (22) to (25), further including: an output unit that outputs information indicating the motion pattern of the user.

(27) The information processing device of any one of (22) to (26), wherein the output unit displays an image or text indicating the motion pattern of the user.

(28) The information processing device of any one of (22) to (27), wherein the analysis unit determines the motion pattern of the user also based on the first time-series data.

(29) The information processing device of any one of (22) to (28), wherein the second sensor includes an acceleration sensor, a gyro sensor, or a geomagnetic sensor.

(30) The information processing device of any one of (22) to (29), wherein the first sensor includes a uniaxial acceleration sensor and the second sensor includes a triaxial acceleration sensor.

(31) A sensor device which is mounted directly or indirectly on a user who plays sports, the sensor device including: a first sensor that detects a shock transferred to the sensor device; a second sensor that detects a physical behavior of the sensor device with a resolution higher than a resolution of the first sensor; and a sensor data preprocessing unit that outputs analysis target data provided for analysis performed to determine a motion pattern of the user based on first time series data including a detected value of the first sensor and second time-series data including a detected value of the second sensor.

(32) The sensor device according to (31), wherein the sensor data preprocessing unit sets an analysis target segment in which the analysis is performed in the second time-series data based on the first time-series data and outputs the second lime-series data in the analysis target segment as the analysis target data.

(33) The sensor device according to (31) or (32), further including: a communication unit that transmits the analysis target data to an analysis device.

(34) An information processing system including: a sensor device that is mounted directly or indirectly on a user who plays sports; and an analysis device that determines a motion pattern of the user by analyzing analysis target data transmitted from the sensor device, wherein the sensor device includes a first sensor that detects a shock transferred to the sensor device, a second sensor that detects a physical behavior of the sensor device with a resolution higher than a resolution of the first sensor, and a sensor data preprocessing unit that generates the analysis target data based on first time-series data including a detected value of the first sensor and second time-series data including a detected value of the second sensor, and a communication unit that transmits the analysis target data to the analysis device, wherein the analysis device includes a communication unit that receives the analysis target data, and an analysis unit that determines the motion pattern of the user based on the analysis target data, wherein one of the sensor device and the analysis device includes a segment setting unit that sets an analysis target segment in the second time-series data based on the first time-series data included in the analysis target data, and wherein the analysis unit determines the motion pattern of the user based on the second time-series data in the analysis target segment.

(35) A non-transitory computer-readable storage medium having a program stored therein, the program causing a computer to execute: a function of acquiring first time-series data including a detected value of a first sensor detecting a shock transferred to a sensor device mounted directly or indirectly on a user who plays sports and second time-series data including a detected value of a second sensor detecting a physical behavior of the sensor device with a resolution higher than a resolution of the first sensor; and a function of setting an analysis target segment in which analysis is performed to determine a motion pattern of the user in the second time-series data based cm the first time-series data.

(36) A non-transitory computer-readable storage medium having a program stored therein, the program causing a computer included in a sensor device mounted directly or indirectly on a user who plays sports to execute: a function of outputting analysis target data provided for analysis performed to determine a motion pattern of the user based on first time-series data including a detected value of a first sensor detecting to shock transferred to the sensor device and second time-series data including a detected value of a second sensor detecting a physical behavior of the sensor device with a resolution higher Hum a resolution of the first sensor.

What is claimed is:

1. A non-transitory computer readable storage device including instructions that when executed by a processor configure the processor to implement an information processing method, the method comprising:
    receiving time-series data from a motion sensor that senses motion of an object;
    identifying a motion pattern of the object as one of plural predetermined motion patterns based on the time-series data from the motion sensor and a stored dictionary defining each of the plural predetermined motion patterns; and
    controlling display of an impact position distribution for each motion pattern identified in the identifying patterns of the object,
    wherein the impact position distribution displays a color corresponding to a frequency of impact occurrence.

2. The non transitory computer-readable medium according to claim 1, the method further comprising: counting with the processor a number of impacts for each motion pattern identified in the identifying.

3. The non-transitory computer-readable medium according to claim 1, the method further comprising:
    displaying a shot type ratio for each motion pattern identified in the identifying.

4. The non-transitory computer-readable medium according to claim 3, wherein
    the controlling display includes controlling display of the shot type ratio according to a color classification.

5. The non-transitory computer-readable medium according to claim 1,
    wherein the controlling display includes displaying at a same time the impact position distribution with a number of impacts.

6. The non-transitory computer-readable medium according to claim 1,
    wherein the controlling display includes displaying the impact position distribution to overlap on a diagram representing an image of sport equipment.

7. The non-transitory computer-readable medium according to claim 1, further comprising determining a shot type by a corresponding motion pattern.

8. The non-transitory computer-readable medium according to claim 7,
    wherein the shot type includes a tennis stroke.

9. The non-transitory computer-readable medium according to claim 8,
    wherein the tennis stroke includes at least one of a forehand, a backhand, a serve, a smash and a volley.

10. An information processing method comprising:
    receiving time-series data from a motion sensor that senses motion of an object;
    identifying a motion pattern of the object as one of plural predetermined motion patterns based on the time-series data from the motion sensor and a stored dictionary defining each of the plural predetermined motion patterns; and
    controlling displaying of an impact position distribution for each motion pattern identified in the identifying,
    wherein the impact position distribution displays a color classification corresponding to a frequency of impact occurrence.

11. The method according to claim 10, further comprising counting with a processor a number of impacts for each motion pattern identified in the identifying.

12. The method according to claim 11, further comprising:
    displaying a shot type ratio for each motion pattern identified in the identifying.

13. The method according to claim 12, wherein
    the controlling displaying includes displaying the shot type ratio according to a color classification.

14. The method according to claim 10,
    wherein the controlling displaying includes displaying at a same time the impact position distribution with a number of impacts.

15. The method according to claim 10,
    wherein the controlling displaying includes displaying the impact position distribution to overlap on a diagram representing an image of sport equipment.

16. The method according to claim 10, further comprising:
    determining a shot type by a corresponding motion pattern, wherein the shot type includes a tennis stroke, and the tennis stroke includes at least one of a forehand, a backhand, a serve, a smash and a volley.

17. An information processing apparatus comprising:
    a computer storage medium that has stored therein a dictionary defining each of a plural predetermined motion patterns; and
    processing circuitry configured to
    receive time-series data from a motion sensor that senses motion of an object;
    identify a motion pattern of the object as one of plural predetermined motion patterns based on the time-series data from the motion sensor and the dictionary defining each of the plural predetermined motion patterns; and
    control display of an impact position distribution for each motion pattern previously identified,
    wherein an impact position distribution displays a color classification corresponding to a frequency of impact occurrence.

18. The information processing apparatus according to claim 17, wherein
    the processing circuitry is further configured to count a number of impacts for each motion pattern previously identified.

19. The information processing apparatus according to claim 17, wherein
    the processing circuitry is further configured to display a shot type ratio for each motion pattern previously identified, wherein the shot type ratio is displayed according to a color classification.

20. The information processing apparatus according to claim 17,
    wherein the processing circuitry is configured to display at a same time the impact position distribution with a number of impacts.

* * * * *